(12) United States Patent
Li et al.

(10) Patent No.: US 9,242,936 B2
(45) Date of Patent: *Jan. 26, 2016

(54) METHODS FOR THE PREPARATION OF CHARGED CROSSLINKERS

(71) Applicant: ImmunoGen, Inc., Waltham, MA (US)

(72) Inventors: Wei Li, Acton, MA (US); Robert Yongxin Zhao, Lexington, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/539,361

(22) Filed: Nov. 12, 2014

(65) Prior Publication Data

US 2015/0166482 A1    Jun. 18, 2015

Related U.S. Application Data

(60) Continuation of application No. 14/045,151, filed on Oct. 3, 2013, now Pat. No. 8,921,566, which is a division of application No. 13/315,005, filed on Dec. 8, 2011, now Pat. No. 8,598,362.

(60) Provisional application No. 61/421,357, filed on Dec. 9, 2010.

(51) Int. Cl.
C07D 401/00 (2006.01)
C07D 213/71 (2006.01)
C07D 207/452 (2006.01)
C07D 207/46 (2006.01)
C07D 401/12 (2006.01)

(52) U.S. Cl.
CPC .......... *C07D 213/71* (2013.01); *C07D 207/452* (2013.01); *C07D 207/46* (2013.01); *C07D 401/12* (2013.01)

(58) Field of Classification Search
None
See application file for complete search history.

(56) References Cited

U.S. PATENT DOCUMENTS

| 2,822,387 | A | 2/1958 | Bloch at al. |
| 3,418,290 | A | 12/1968 | Bantjes at al. |
| 4,244,885 | A | 1/1981 | Nudelman et al. |
| 5,534,651 | A | 7/1996 | Quittmann et al. |
| 5,783,710 | A | 7/1998 | Bauer et al. |
| 8,598,362 | B2 * | 12/2013 | Li et al. ............ 546/278.1 |
| 2004/0039176 | A1 | 2/2004 | Widdison |
| 2009/0274713 | A1 | 11/2009 | Chari et al. |

FOREIGN PATENT DOCUMENTS

| DE | 800410 C | 11/1950 |
| WO | WO-03/094845 A2 | 11/2003 |

OTHER PUBLICATIONS

International Search Report issued in PCT/US2011/63944 on Apr. 19, 2012 (in the name of Immunogen, Inc.).
Zhao et al.; "Synthesis and Evaluation of Hydrophilic Linkers for Antibody-Maytansinoid Conjugates:" J. Med. Chem.; 54(10):3606-3623 [XP055046274](May 26, 2011).
Le Berre et al.; "Acides alpha-sulfocarboxyliques at dêrivês. II. Clorosulfonylation de la gamma-butyrolactone at de l'anhydride maléique;" Bull. Soc. Chim. Fr.; 1:214-218 [XP000177149](1973).

* cited by examiner

*Primary Examiner* — Heidi Reese
(74) *Attorney, Agent, or Firm* — McCarter & English, LLP; Steven G. Davis; Xin Zhang

(57) ABSTRACT

Processes for the preparation of charged crosslinkers bearing a sulfonic acid moiety are disclosed. These procedures also optionally include methods to convert the resulting products to substantially a single salt form.

33 Claims, 16 Drawing Sheets

Structure of sulfo-SPDB and Antibody-Drug conjugate

Sulfo-SPDB 1a

Antibody-(sulfo-SPDB)-DM4

FIG. 1 Structures of representative non-charged crosslinkers (PRIOR ART)
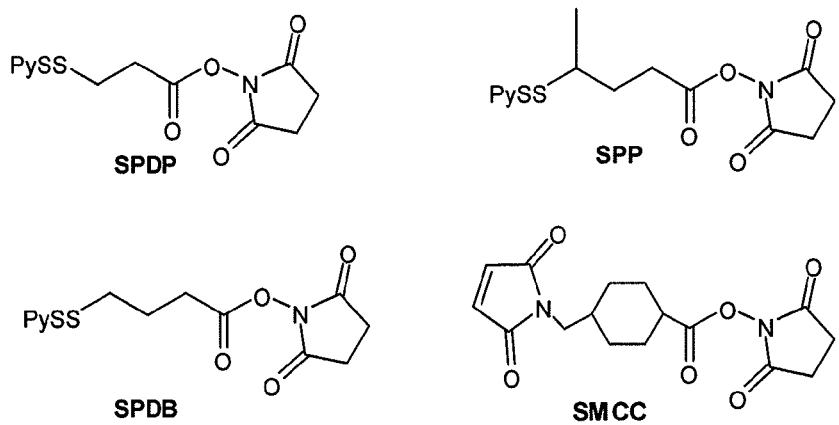
FIG. 2 Structure of sulfo-SPDB and Antibody-Drug conjugate
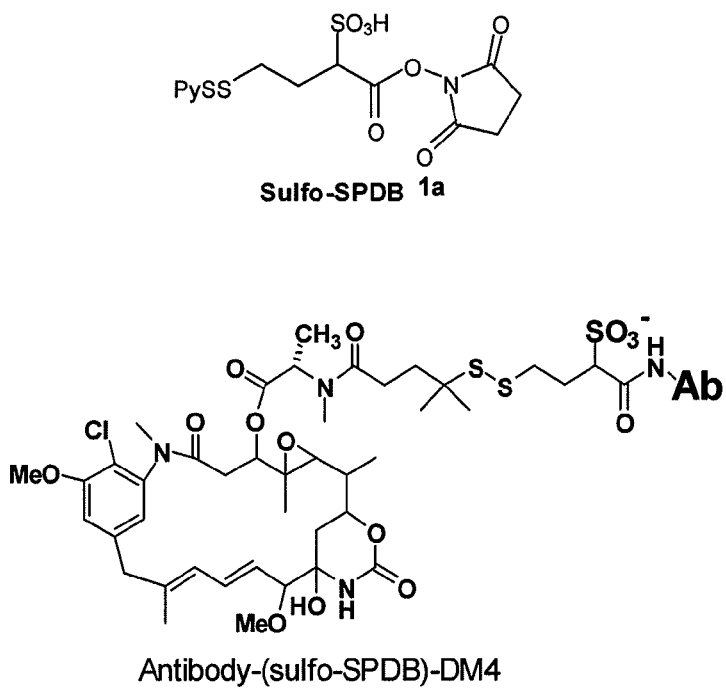

FIG. 3 Synthesis of sulfo-SPDB (PRIOR ART)
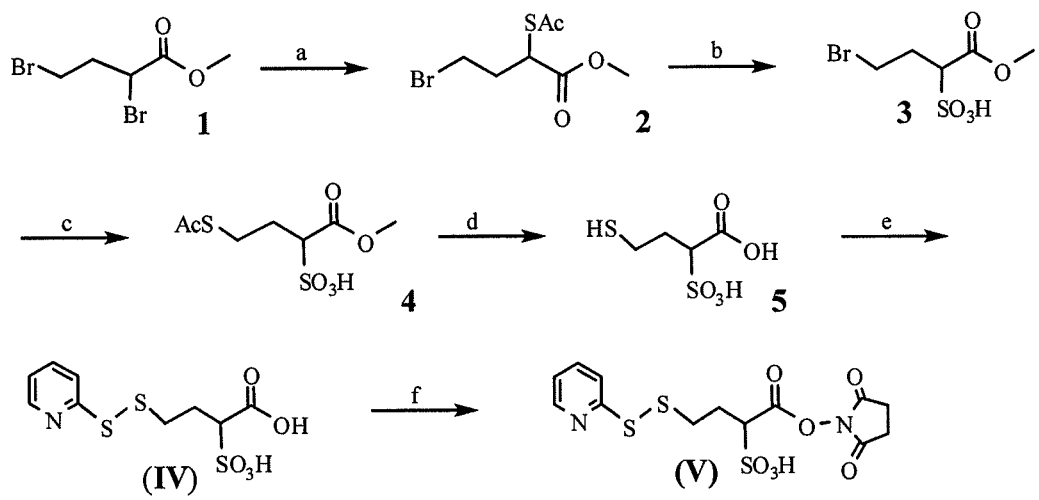
Conditions: (a) HSAc, DIPEA, THF, -20°C (b) H$_2$O$_2$/HOAc; (c) HSAc, DIPEA, DMA;
(d) NaOH; (e) (SPy)$_2$, pH 7.5; (f) NHS, EDC, DMA, 82%;

FIG. 4 New synthesis of sulfo-SPDB
a)
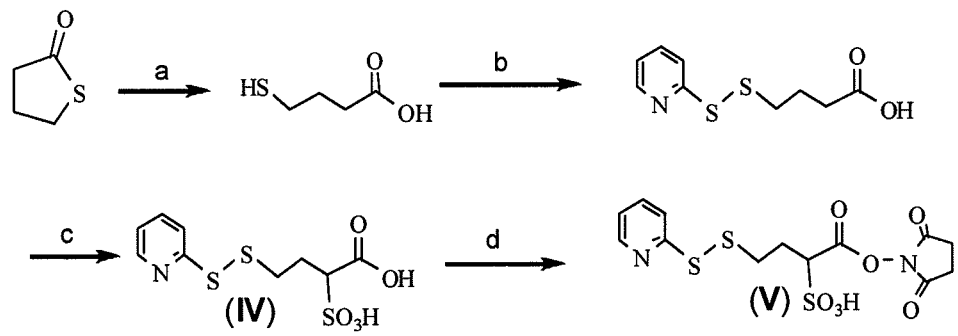
Conditions: (a) NaOH ; (b) PySSPy; (c) ClSO$_3$H, ClCH$_2$CH$_2$Cl +/- base
(d) NHS, EDC
b)
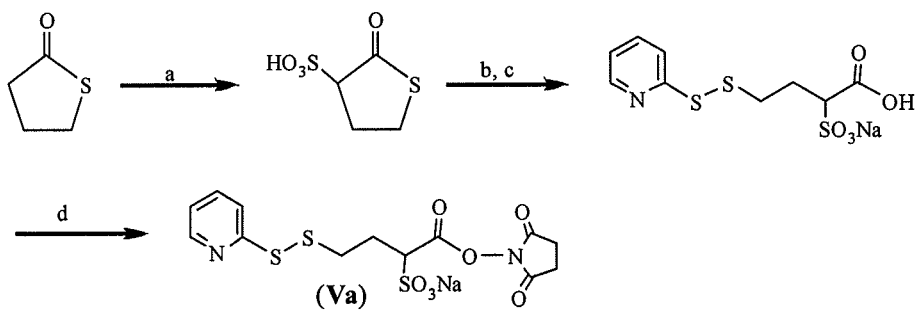
Conditions: (a) ClSO$_3$H/DIPEA; (b) 0.5 M NaOH; (c) pH 7, PySSPy;
(d) NHS, EDC, DMA

FIG. 5 Synthesis of disulfide-containing crosslinking agents
a)
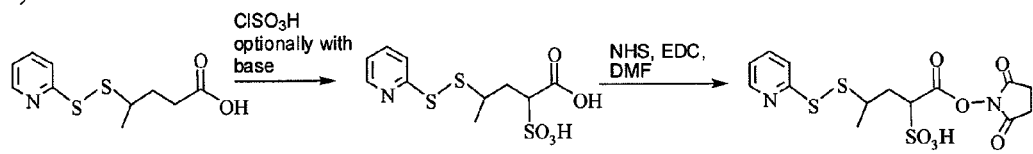
b)
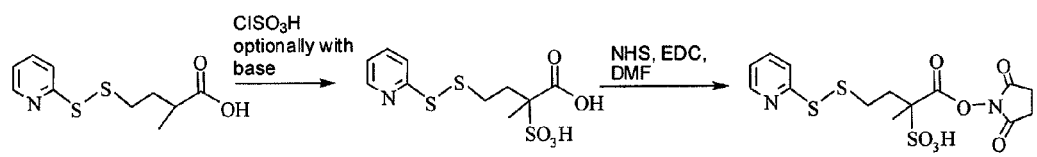
c)
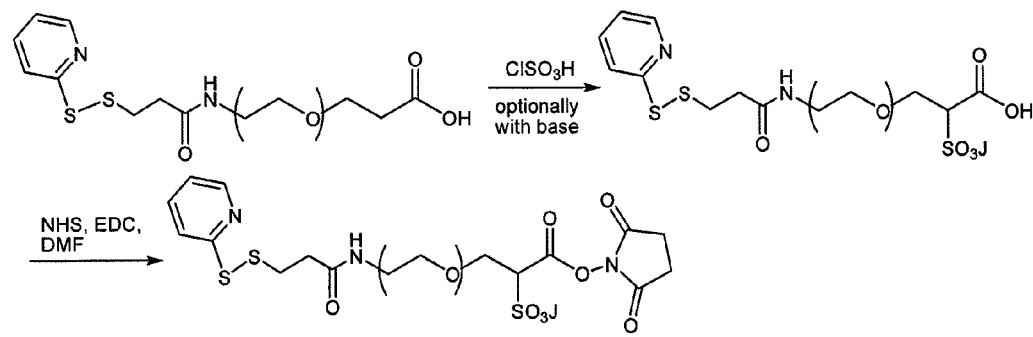

d) FIG. 5 - Continued
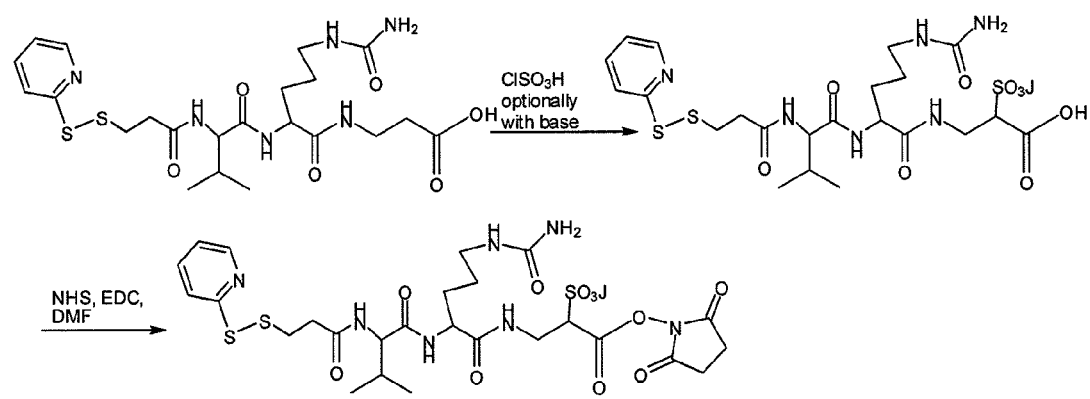
e)
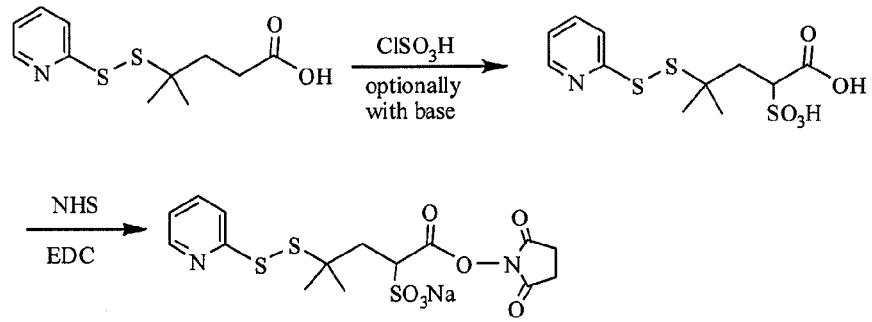

FIG. 6 Synthesis of maleimide-based cross linking agents.
a)
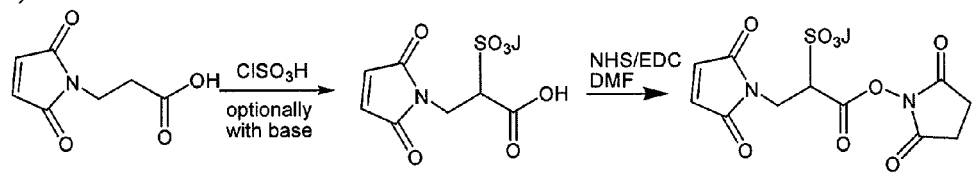
b)
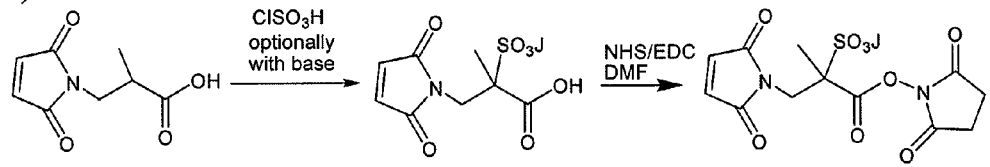
c)
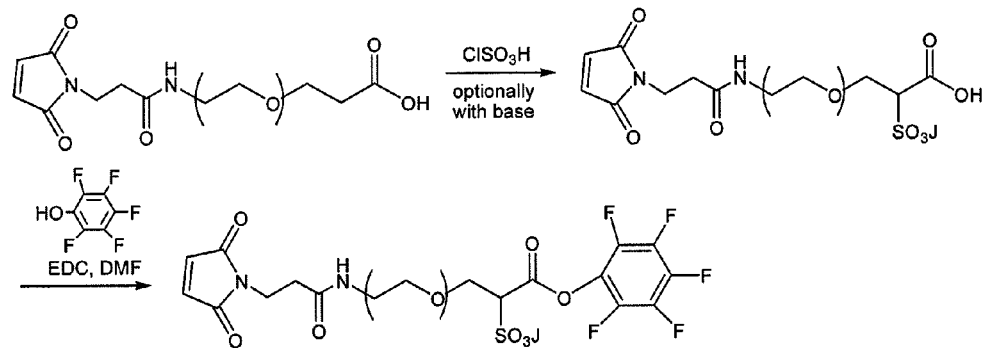

FIG. 6 - Continued
d)
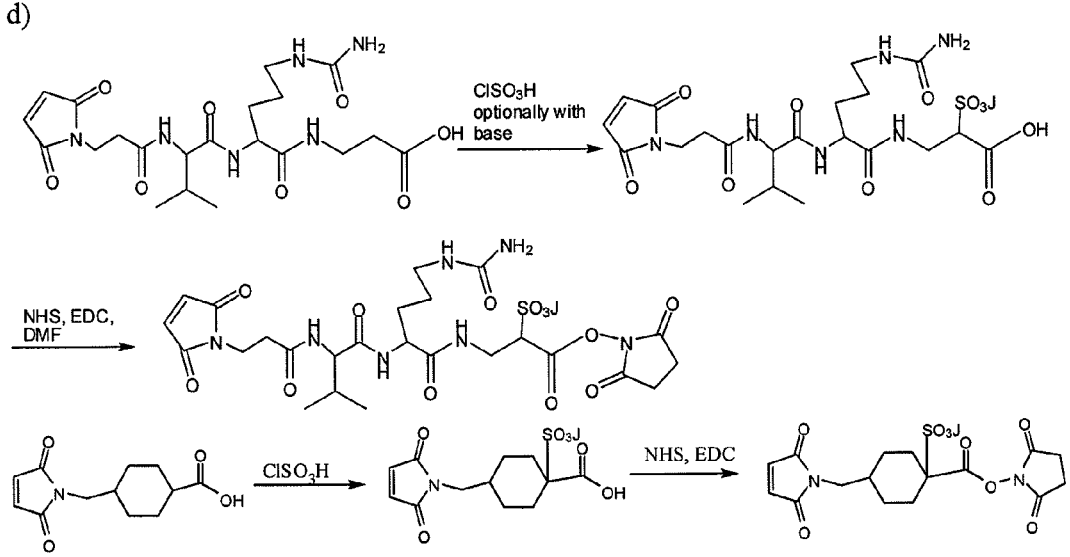

FIG. 7 Synthesis of haloacetamido-based crosslinking agents
a)
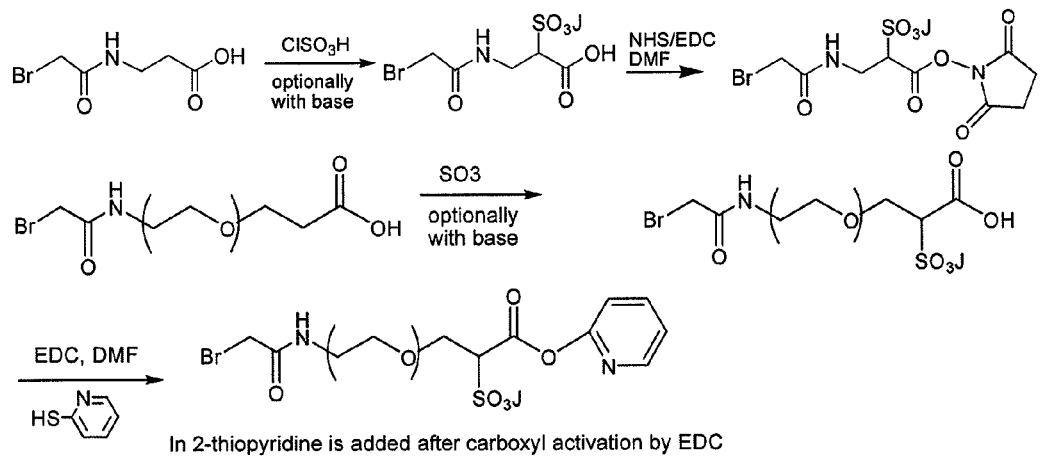
b)
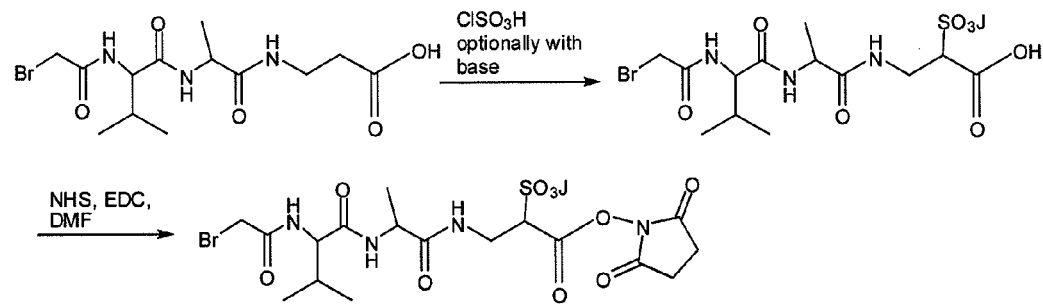

US 9,242,936 B2

METHODS FOR THE PREPARATION OF CHARGED CROSSLINKERS

REFERENCE TO RELATED APPLICATIONS

This application is a continuation application of U.S. Ser. No. 14/045,151, now allowed, filed on Oct. 3, 2013; which is a divisional application of U.S. Ser. No. 13/315,005, filed on Dec. 8, 2011, issued as U.S. Pat. No. 8,598,362 on Dec. 3, 2013, which claims the benefit of the filing date under 35 U.S.C. §119(e) of U.S. Provisional Application No. 61/421,357, filed on Dec. 9, 2010, the entire content of each of the applications is incorporated herein by reference.

FIELD OF THE INVENTION

The present invention relates to a process of preparing sulfonic acid-bearing crosslinkers. The sulfonic acid moiety can be a free acid or a salt or a mixture of free acid and salts. These linkers are used to prepare conjugates by covalently attaching two entities together, in which one entity contains an amino or a hydroxyl group and the other entity contains a thiol group. The sulfonic acid moiety of these linkers improves the aqueous solubility of the resulting conjugates.

BACKGROUND OF THE INVENTION

Compounds that can link together a thiol-bearing moiety and an amine-bearing moiety have found use in many diverse applications such as the linkage of cytotoxic agents, fluorophores or metal chelating agents to cell binding agents such as antibodies, growth factors or vitamins, or to large complexes such as liposomes (see U.S. Pat. Nos. 5,208,020; 5,416,064; 5,846,545; 6,340,701; 6,716,821; 7,217,819; 7,276,497; 7,388,026; 7,598,290 and U.S. Patent Publication No. 20100203007). Examples of such linkers include SPP, SPDP, SPDB and SMCC (FIG. 1) (see U.S. Pat. Nos. 4,563,304; 6,913,748; 7,276,497; Widdison et al., 2006, *J. Med. Chem.*, 49, 4392-4408; Phillips et al., 2008 *Cancer Res.*, 68, 9280-9290). Often one or both of the entities that are to be linked together have only limited solubility in water which results in poor aqueous solubility of the resulting conjugate.

Recently, it has been shown that antibody-drug conjugates, wherein the antibody and the cytotoxic drug were linked via charged crosslinkers, especially those that comprise a sulfonic acid substituent showed several benefits over the corresponding conjugates prepared with non-charged linkers (FIG. 2). These benefits include a) greater aqueous solubility of the antibody-drug conjugate, b) ability to increase the drug load on the antibody, while maintaining solubility and monomer content and c) greater therapeutic activity, especially toward multidrug resistant cells (see U.S. Patent Publication No. 20090274713 & 20100129314). Improved pre-clinical efficacy of antibody-drug conjugates prepared with the sulfo-SPDB crosslinker [FIG. 2, compound (V)] that comprises a sulfonic acid substituent, has also been recently reported (Kovtun et al., 2010 European J. Cancer, Suppl, 8, p 76, Abstract #235). The only previously reported synthesis of sulfo-SPDB is a lengthy and inefficient process comprising of 6 chemical steps (FIG. 3, see U.S. Patent Publication No. 20090274713). Thus there is a need to provide a simplified and scalable process for the preparation of charged crosslinkers, such as sulfo-SPDB, that comprise a sulfonic acid group. These and other needs are addressed in the current invention.

SUMMARY OF THE INVENTION

The present invention describes processes for preparing sulfonic acid-bearing heterobifunctional linkers. These linkers bear a thiol-reactive moiety to link one component, such as a cytotoxic drug, via a disulfide bond or a thioether bond, and an amine- or hydroxyl-reactive moiety to link a second component, such as a cell binding agent, via an amide or ester bond. The sulfonic acid moiety of these linkers is located on the carbon alpha to the carbon bearing the amine or hydroxyl-reactive moiety and can exist as a free sulfonic acid, or as a salt. The invention also encompasses the conversion of the sulfonic acid in free acid or an undesired salt form to a substantially specific desired salt form such as a sodium salt or a potassium salt.

DESCRIPTION OF THE FIGURES

FIG. 1 shows the structures of previously described non-charged linkers.

FIG. 2 shows the structures of sulfo-SPDB and an antibody-drug conjugate prepared with sulfo-SPDB.

FIG. 3 shows the synthesis of sulfo-SPDB from the prior art.

FIG. 4 shows the synthesis of sulfo-SPDB using the new method.

FIG. 5 shows the synthesis of disulfide-containing α-sulfonic acid crosslinking agents. J is H or a cation described herein.

FIG. 6 shows the synthesis of maleimide-containing α-sulfonic acid crosslinking agents. J is H or a cation described herein.

FIG. 7 shows the synthesis of haloacetamido-containing α-sulfonic acid crosslinking agents. J is H or a cation described herein.

DETAILED DESCRIPTION OF THE INVENTION

Figure 8:
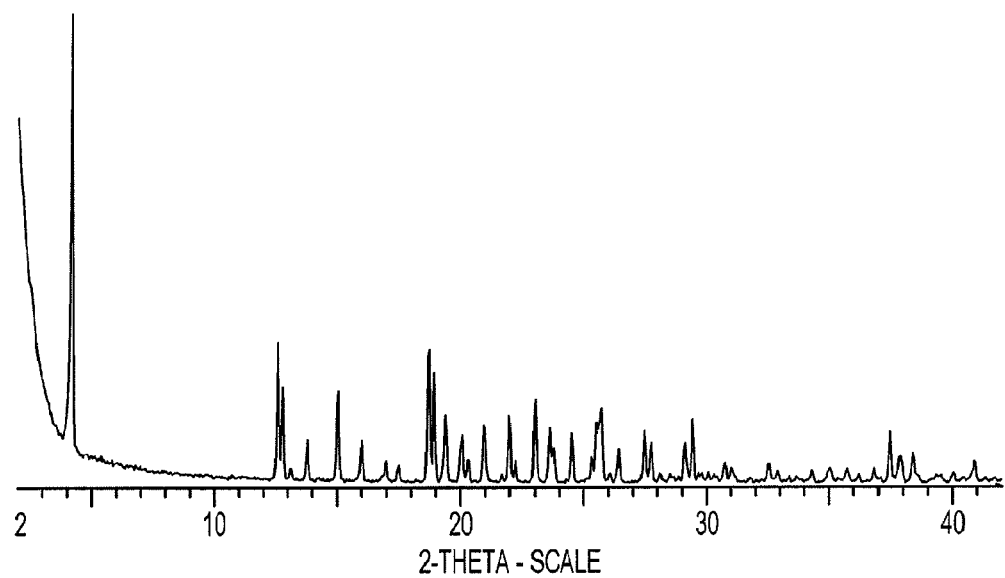
FIG. 8 shows the X-ray powder diffraction pattern of Crystalline Form 1 of compound (V).

The invention discloses methods for the preparation of compounds that comprise a thiol reactive group, a sulfonic acid substituent and a carboxylic acid or a carboxylic acid derivative that is capable of reacting with an amine or a hydroxyl group. Compounds that can be prepared by the process described herein are represented by formula (I) and (III):

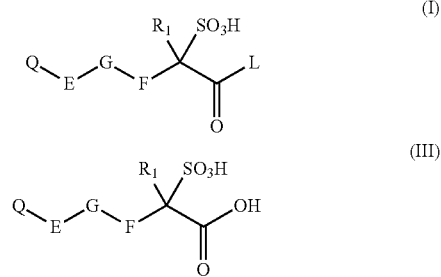

or a salt thereof, wherein,

Q represents a thiol-reactive moiety. In one embodiment, Q is a disulfide group selected from, but not limited to, alkyl disulfide, phenyl disulfide, ortho or para-nitrophenyl disulfide, 2,4-dintrophenyl disulfide, pyridyl disulfide, nitropyridyl disulfide; a maleimido group, a haloacetyl group or haloacetamido group. Preferably, Q is selected from a pyridyl disulfide, a nitropyridyl disulfide, a maleimido, a bromoacetamido or iodoacetamido group. More preferably, Q is selected from a pyridyl disulfide or a maleimido group. Still more preferably, Q is a pyridyl disulfide.

E represents a linear, branched or cyclic alkyl, alkenyl or alkynyl having 1 to 10 carbon atoms, a phenyl group, a three to six membered heterocycloalkyl group or a five or six-membered heteroaromatic group, containing 1, 2 or 3 heteroatoms selected from O, N or S. Preferably, E is selected from a linear, branched or cyclic alkyl containing 1 to 6 carbon atoms, a phenyl or a piperidine group. More preferably, E is a linear alkyl having 1 to 4 carbon atoms. Still more preferably, E is represented by —CH$_2$CH$_2$—.

F is an optional moiety that has the same definition as E. Preferably, F is a linear or branched alkyl having 1 to 4 carbon atoms. Still more preferably, F is absent.

Alternatively, when G is absent, F and R$_1$ together with the carbon atom from which they are attached can form a three to seven membered cycloalkyl group. Preferably, the cycloalkyl group is a cyclohexyl group.

G is absent or represents -G'-(OCH$_2$CH$_2$)$_n$ or -G'-(CH$_2$CH$_2$O)$_n$, wherein n is 0 or an integer from 1 to 24; G' is absent, —C(=O)NR$_2$— or —NR$_2$C(=O)—; and R$_2$ is H or a linear, branched or cyclic alkyl having 1 to 10 carbon atoms. In one embodiment, G is —C(=O)NR$_2$—(CH$_2$CH$_2$O)$_n$, wherein n is 0 or an integer from 1 to 5. In a preferred embodiment, R$_2$ is H or Me. In another preferred embodiment, n is 2 or 4. Alternatively, G is an amino acid or a peptide unit, represented by -(AA)$_m$-, wherein AA is an amino acid residue; and m is 0 or an integer from 1 to 6. In one embodiment, when m is 1, AA is preferably glycine or alanine. In another embodiment, m is 2 or 3. Preferably, G is gly-gly or gly-gly-gly. Even more preferably, G is absent.

R$_1$ is H or linear, branched or cyclic alkyl, alkenyl or alkynyl having 1 to 10 carbon atoms. Preferably, R$_1$ is selected from H or a linear or branched alkyl having 1 to 4 carbon atoms. More preferably, R$_1$ is H.

C(=O)L is a reactive ester or thioester group. In one embodiment, the reactive ester or thioester group is selected from but not limited to an N-hydroxysuccinimide ester, N-hydroxy sulfosuccinimide ester, nitrophenyl ester, tetrafluoro phenyl ester, pentafluorophenyl ester, a thiopyridyl ester a thionitrophenyl ester. Preferably, the reactive ester group is an N-hydroxysuccinimide ester.

In one embodiment, for compounds of formula (I) and (III), G and F are both absent, E is a linear or branched alkyl bearing 1 to 4 carbon atoms. Preferably, E is —CH$_2$—CH$_2$—.

In another embodiment, for compounds of formula (I) and (III), G is absent and F and R$_1$ together forms a three to seven membered cycloalkyl group. Preferably, the cycloalkyl group is cyclohexyl. More preferably, E is a linear or branched alkyl bearing 1 to 4 carbon atoms. Even more preferably, E is —CH$_2$—.

One embodiment of the invention discloses a process for the preparation of compounds of formula (III):

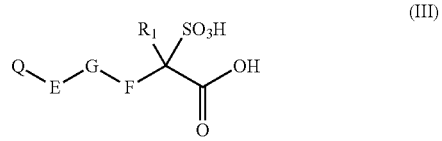

or a salt thereof, comprising the following steps:

a) reacting a compound of formula (II)

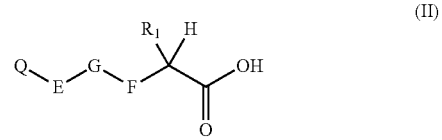

or a salt thereof, with a sulfonating agent optionally in the presence of a base to provide the compound of formula (III); wherein the definitions of Q, E, G, F and R$_1$ are as indicated above. Preferably, the sulfonating agent is selected from, but not limited to, chlorosulfonic acid and sulfur trioxide. More preferably, the sulfonating agent is chlorosulfonic acid. Preferably, the base is selected from, but not limited to, trialkylamine, such as triethyl amine, diisopropylethyl amine or tributyl amine, or 4-alkylmorpholine, such as 4-methylmorpholine. More preferably, the base is diisopropylethyl amine;

b) Optionally purifying the product. Purification methods are known in the art and include chromatography and/or crystallization. Suitable forms of chromatographic purification include but are not limited to solid/liquid chromatography such as flash chromatography, medium pressure chromatography, or high pressure liquid chromatography (HPLC), including normal phase, reverse phase, ion pair and ion exchange chromatography, super critical chromatography and forms of liquid/liquid chromatography such as counter current chromatography, droplet countercurrent chromatography, centrifugal partition chromatography, high speed countercurrent chromatography, or a combination of the above in any order. Preferably, the product is purified by reverse phase chromatography.

A second embodiment of the invention discloses a process for the preparation of compounds of formula (I) or a salt thereof, comprising the following steps:

a) reacting a compound of formula (II)

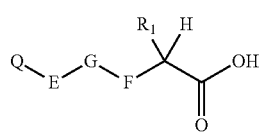

(II)

or a salt thereof, with a sulfonating agent optionally in the presence of a base to provide the compound of formula (III) or a salt thereof; wherein the definitions of Q, E, G, F and $R_1$ are as indicated above. Preferably, the sulfonating agent is selected from, but not limited to, chlorosulfonic acid and sulfur trioxide. More preferably, the sulfonating agent is chlorosulfonic acid. Preferably, the base is selected from, but not limited to, trialkylamine, such as triethyl amine, diisopropylethyl amine (DIPEA) or tributyl amine, or 4-alkylmorpholine, such as 4-methylmorpholine. More preferably, the base is diisopropylethyl amine.

b) Optionally purifying the product. Purification methods are known in the art and include chromatography and/or crystallization. Suitable forms of chromatographic purification include but are not limited to solid/liquid chromatography such as flash chromatography or high pressure liquid chromatography (HPLC), including normal phase, reverse phase, ion pair and ion exchange chromatography, super critical chromatography and forms of liquid/liquid chromatography such as counter current chromatography, droplet countercurrent chromatography, centrifugal partition chromatography, high speed countercurrent chromatography, or a combination of the above in any order. Preferably, the product is purified by reverse phase chromatography.

c) Reacting the carboxylic acid moiety of the product of formula (III) or a salt thereof with a hydroxy or mercapto compound in the presence of a coupling reagent to provide the compound of formula (I) or a salt thereof. Preferably, the hydroxy or mercapto compound is selected from, but not limited to, N-hydroxysuccinimide, N-hydroxy sulfo-succinimide, tetrafluorophenol, nitrophenol, dinitrophenol or thiopyridine. More preferably, the hydroxyl or mercapto compound is N-hydroxysuccinimide. Preferably, the coupling agent is selected from, but not limited to N,N'-dicyclohexylcarbodiimide (DCC), 1-ethyl-3-(3-dimethylaminopropyl) carbodiimide (EDC), N,N'-diisopropyl carbodiimide (DIC), 1-ethoxycarbonyl-2-ethoxy-1,2-dihydroquinoline (EEDQ). More preferably, the coupling agent is EDC.

d) Optional purification of the resulting compound of formula (I) by chromatographic methods and/or crystallization by the methods listed above.

The schematic representation of the process steps are below:

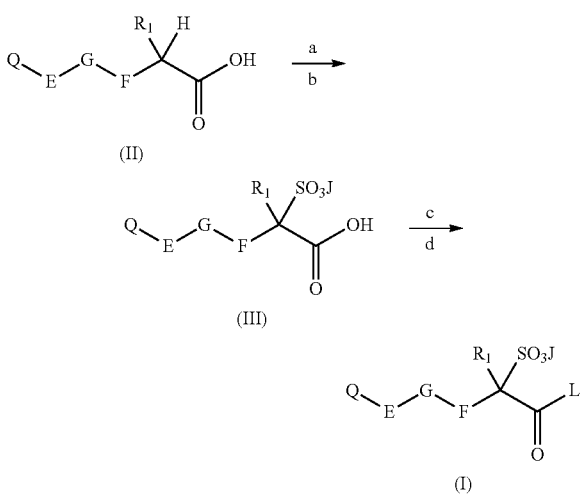

a = ClSO$_3$H of SO$_3$/ +/- base
b = optional purification
c = X + coupling agent
d = optional purification wherein, the definitions are as above; X is selected from N-hydroxysuccinimide, N-hydroxy sulfo-succinimide, tetrafluorophenol, nitrophenol, dinitrophenol or thiopyridine; and J is H or a salt cation described herein.

A third embodiment provides a process for the preparation of a compound of formula (IV):

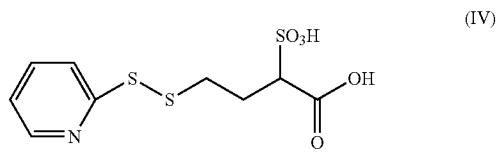

or a salt thereof, comprising:

a) reacting 4-(2-pyridyldithio)butanoic acid (2a) or a salt thereof with a sulfonating agent, optionally in the presence of a base to provide 4-(2'-pyridyldithio)-2-sulfo-butanoic acid (IV) or a salt thereof. Preferably, the sulfonating agent is selected from chlorosulfonic acid or sulfur trioxide. More preferably, the sulfonating agent is chlorosulfonic acid. Preferably, the base is selected from, but not limited to, triethyl amine, diisopropylethyl amine or tributyl amine. More preferably, the base is diisopropylethyl amine.

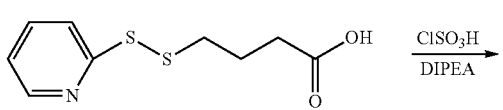

2a

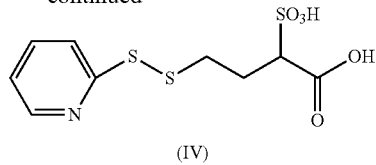

(IV)

In one embodiment, the reaction of compound (2a) or a salt thereof with a sulfonating agent is carried out in the presence of 1,2-di(pyridin-2-yl)disulfane (PySSPy). An amount of about 0.1 to about 5.0 equivalent, preferably about 0.5 to about 1.0 equivalent of PySSPy relative to compound (2a) can be used. Preferably, about 0.5 equivalent (e.g., 0.4, 0.5, 0.6 equivalent) of PySSPy can be used.

A fourth embodiment provides a process for the preparation of a compound of formula (V):

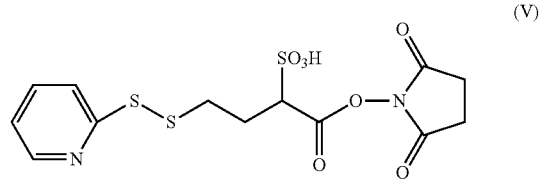

or a salt thereof, comprising:

a) reacting 4-(2-pyridyldithio)butanoic acid (2a) or a salt thereof with a sulfonating agent, optionally in the presence of a base to provide 4-(2'-pyridyldithio)-2-sulfo-butanoic acid (IV) or a salt thereof. Preferably, the sulfonating agent is selected from chlorosulfonic acid or sulfur trioxide. More

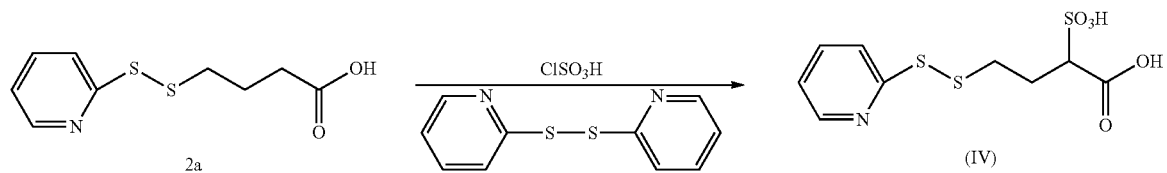 [SMILES: O=C(O)CCCSSc1ccccn1 ; c1ccc(SSc2ccccn2)nc1 ; "ClSO3H" ; O=C(O)C(CCSSc1ccccn1)S(=O)(=O)O ; "(IV)"]

Alternatively, PySSPy can be added after the reaction or during the workup of the reaction, such as during the extraction of the product from the reaction mixture.

4-(2-pyridyldithio)butanoic acid (2a) can be prepared according to known procedures in the art, such as those described in Widdison W C et al. Semisynthetic maytansine analogues for the targeted treatment of cancer. J Med Chem. 2006; 49:4392-4408, the entire teaching of which is incorporated by reference herein by its entirety.

b) Optional purification by chromatography and/or crystallization. In one embodiment, the compound of formula (IV) is purified by chromatography. Suitable forms of chromatographic purification can be determined by one of ordinary skill in the art and include, but are not limited to those described above. Preferably, the chromatography is reverse phase chromatography. In another preferred embodiment, the compound of formula (IV) is purified on a silica column using a suitable eluting solvent or solvents. In a more preferred embodiment, the compound of formula (IV) is purified on silica column using a mixture of water and one or more organic solvents as the eluting solvent. For example, the eluting solvent can be a mixture of water and acetonitrile, optionally with a small amount of an acid, e.g., acetic acid. In a more specific embodiment, the eluting solvent is a mixture of water, acetonitrile and acetic acid in a volume ratio of 1:10:0.01.

preferably, the sulfonating agent is chlorosulfonic acid. Preferably, the base is selected from, but not limited to, triethyl amine, diisopropylethyl amine or tributyl amine. More preferably, the base is diisopropylethyl amine.

In one embodiment, the reaction of compound (2a) or a salt thereof with a sulfonating agent is carried out in the presence of 1,2-di(pyridin-2-yl)disulfane (PySSPy). An amount of about 0.1 to about 5.0 equivalent, preferably about 0.5 to about 1.0 equivalent of PySSPy relative to compound (2a) can be used. Preferably, about 0.5 equivalent (e.g., 0.4, 0.5 or 0.6 equivalent) of PySSPy can be used.

Alternatively, PySSPy can be added after the reaction or during the workup of the reaction, such as during the extraction of the product from the reaction mixture.

b) Optional purification by chromatography and/or crystallization. In one embodiment, the compound of formula (IV) is purified by chromatography. Suitable forms of chromatographic purification can be determined by one of ordinary skill in the art and includes, but is not limited to those described above. Preferably, the purification is by reverse phase chromatography. In another preferred embodiment, the compound of formula (IV) is purified on a silica column using a suitable eluting solvent. In a more preferred embodiment, the compound of formula (IV) is purified on silica column using a mixture of water and organic solvent as the eluting solvent. For example, the eluting solvent can be a mixture of water and acetonitrile, optionally with a small amount of an acid, e.g., acetic acid. In a more specific embodiment, the eluting solvent is a mixture of water, acetonitrile and acetic acid in a volume ratio of 1:10:0.01.

c) Reacting the carboxylic acid moiety of the compound of formula (IV) or a salt thereof with N-hydroxysuccinimide (NHS) in the presence of a coupling reagent to provide the compound of formula (V). Preferably, the coupling agent is selected from, but not limited to N,N'-dicyclohexylcarbodiimide (DCC), 1-ethyl-3-(3-dimethylaminopropyl)carbodiimide (EDC), N,N'-diisopropyl carbodiimide (DIC), 1-ethoxycarbonyl-2-ethoxy-1,2-dihydroquinoline (EEDQ). More preferably, the coupling agent is EDC.

In one embodiment, the reaction of compound of formula (IV) with N-hydroxysuccinimide is carried out in the presence of a base. Preferably, the base is selected from, but not limited to, trialkylamine, such as triethyl amine, diisopropylethyl amine or tributyl amine, or 4-alkylmorpholine, such as 4-methylmorpholine. More preferably, the base is diisopropylethyl amine.

d) Optional purification of the resulting compound of formula (V) by chromatographic methods and/or crystallization by the methods listed above.

In one embodiment, the compound of formula (V) is purified by chromatographic methods described herein. In a particular embodiment, the compound of formula (V) is purified on a silica column using an eluting solvent. The eluting solvent optionally contains a small amount of a non-nucleophilic base, which includes, but is not limited to, a trialkylamine, such as triethyl amine, diisopropylethyl amine or tributyl amine, or 4-alkylmorpholine, such as 4-methylmorpholine. Preferably, the base is diisopropylethyl amine. In another embodiment, an ion exchange column can be used to further purify the compound of formula (V) following a purification on a silica column, particularly when a base is used in the reaction of compound of formula (IV) with NHS to form the compound of formula (V) or when a non-nucleophilic base is added after the reaction, during the workup or during the purification of compound (V). Suitable cation exchange columns are well known in the art, for example, those described in Sigma-Aldrich or Supelco catalogs. In one embodiment, the cation exchange resins are Amberlyst® 15 or Dowex® 50WX4-200 resins.

In another embodiment, the compound of formula (V) is purified by crystallization. In one embodiment, the crystallization is carried out by dissolving the compound of formula (V) in a hydrophilic solvent or solvents, followed by placing the resulting solution at a reduced temperature, for example, between about 0° C. to about 10° C., below 0° C., between about −10° C. to about 0° C., between about −20° C. to about −10° C., between about −30° C. to about −20° C., about −10° C., about −20° C. or about −30° C. Preferably, the reduced temperature is about −20° C. Any suitable hydrophilic solvent can be used. Exemplary hydrophilic solvents include, but are not limited to, acetone, dimethyl formamide (DMF), dimethyl sulfoxide (DMSO), acetonitrile and a mixture thereof. Preferably, the hydrophilic solvent is acetone or acetonitrile.

In another embodiment, the compound of formula (V) can be purified by crystallization in a mixture of organic solvent and water. Any suitable organic solvents can be used. For example, the organic solvent can be a water miscible solvent, such as acetone, DMF, DMSO, acetonitrile or a mixture thereof. In a preferred embodiment, crystallization solvent is a mixture of acetone and water. More specifically, the ratio of acetone and water is from about 80:20 v/v to about 99:1. Even more specifically, the volume ratio of acetone to water is 90:10 or 95:5. Crystallization can be carried out by dissolving the compound of formula (V) in the solvent mixture, followed by placing the resulting solution at a reduced temperature, for example, between about 0° C. to about 10° C., below 0° C., between about −10° C. to about 0° C., between about −20° C. to about −10° C., between about −30° C. to about −20° C., about −10° C., about −20° C. or about −30° C. Preferably, the reduced temperature is about −20° C.

In another embodiment, the compound of formula (V) can exist in a salt form, for example, when the reaction of compound of formula (IV) with N-hydroxysuccinimide is carried out in the presence of a base or when a non-nucleophilic base is added after the reaction, during the workup of the reaction or during the purification of compound (V). In one embodiment, the compound of formula (V) is a triethylamine salt, a diisopropylethyl amine salt or a 4-methylmorpholine salt, preferably a diisopropylethylamine salt. The neutral form of the compound can be prepared by passing the salt through an ion exchange column as described above. Alternatively, the neutral form of the compound can be prepared by crystallization of the above-described salts in an organic solvent or a mixture of an organic solvent and water in the presence of a small amount of an acid. Any suitable acid can be used. Exemplary acids include, but are not limited to, trifluoroacetic acid (TFA), HCl, and $H_2SO_4$. Preferably, the acid is HCl or $H_2SO_4$. Any suitable amount of the acid can be used. For example, about 0.1 to 5 equivalent of the acid can be used. Preferably, about 0.1 to about 1.5 equivalent of the acid is used. Even more preferably, about 0.5 to about 1.0 equivalent of the acid is used. Crystallization can be carried out in a suitable organic solvent or organic solvents. Exemplary organic solvents include, but are not limited to, acetone, DMF, DMSO and acetonitrile. Preferably, acetone or acetonitrile are used for crystallization. Alternatively, crystallization can be carried out in a mixture of an organic solvent and water. For example, acetone/water, DMF/water, DMSO/water and acetonitrile/water mixture can be used for crystallization.

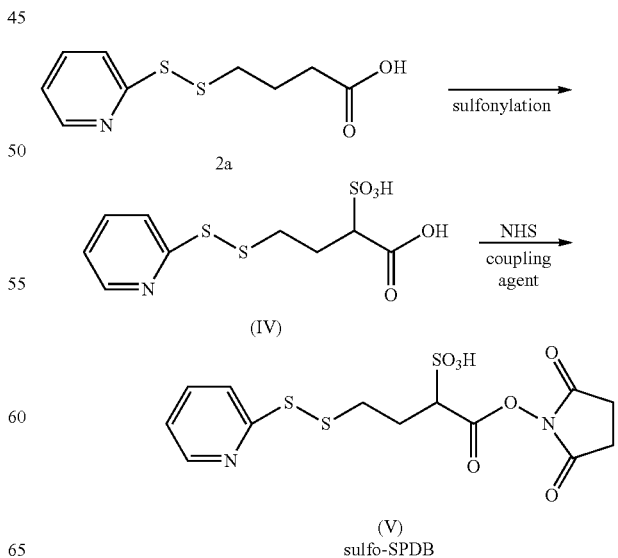

In one embodiment, the invention is directed to new crystalline forms of the compound of formula (V), e.g., Crystalline Forms 1, 2a, 2b and 3 as described below. Compound of formula (V) made according to the procedure described in US 20090274713 is an amorphous solid and is highly hygroscopic. Crystalline Forms 1, 2a, 2b and 3, particularly, crystalline Forms 1, 2a and 2b, are significantly less hygroscopic than the amorphous solid.

Crystalline Forms of Compound of Formula (V)

Crystalline Form 1

In one embodiment, at least a particular percentage by weight of the compound of formula (V) is the Crystalline Form 1 of the compound. Particular weight percentages include 70%, 72%, 75%, 77%, 80%, 82%, 85%, 87%, 88%, 89%, 90%, 91%, 92%, 93%, 94%, 95%, 96%, 97%, 98%, 99%, 99.5%, 99.9%, 100% or a percentage between 70% and 100%.

As used herein, "crystalline" refers to a solid having a highly regular chemical structure. When a particular percentage by weight of the compound of formula (V) is a particular crystalline form, the remainder is some combination of amorphous form and/or one or more crystalline forms other than the particular form that is specified.

Crystalline Form 1 is characterized by the X-ray powder diffraction (XRPD) pattern shown in FIG. 8 with values of 2θ angle and relative intensities as listed in Table 1, obtained using Cu Kα radiation. In a particular embodiment, Form 1 is characterized by one, two, three, four, five, six, seven, eight or nine major XRPD peaks at 2θ angles of 4.2, 12.6, 12.8, 13.8, 15, 20.1, 23, 25.5 and 37.5°. In another embodiment, Form 1 is characterized by major XRPD peaks at 2θ angles of 12.6, 12.8, 15 and 23. It is to be understood that a specified 2θ angle means the specified value ±0.1°.

TABLE 1

Characteristic peaks of Form 1.

| 2θ angle (°) | Intensity % |
|---|---|
| 4.2 | 100 |
| 12.6 | 31.1 |
| 12.8 | 22.1 |
| 13.8 | 10.2 |
| 15 | 20.8 |
| 16 | 10 |
| 18.7 | 29.4 |
| 18.9 | 24.4 |
| 19.4 | 15.9 |
| 20.1 | 12.2 |
| 21 | 13.6 |
| 22 | 15.9 |
| 23 | 19.1 |
| 23.6 | 12.9 |
| 24.5 | 11.9 |
| 25.5 | 14.6 |
| 25.7 | 17.2 |
| 27.5 | 12.2 |
| 27.8 | 9.5 |
| 29.1 | 9.8 |
| 29.4 | 14.3 |
| 37.5 | 11.6 |

As used herein, "major XRPD peak" refers to an XRPD peak with relative intensity greater than 10%. Relative intensity is calculated as a ratio of the peak intensity of the peak of interest versus the peak intensity of the largest peak.

Figure 9:
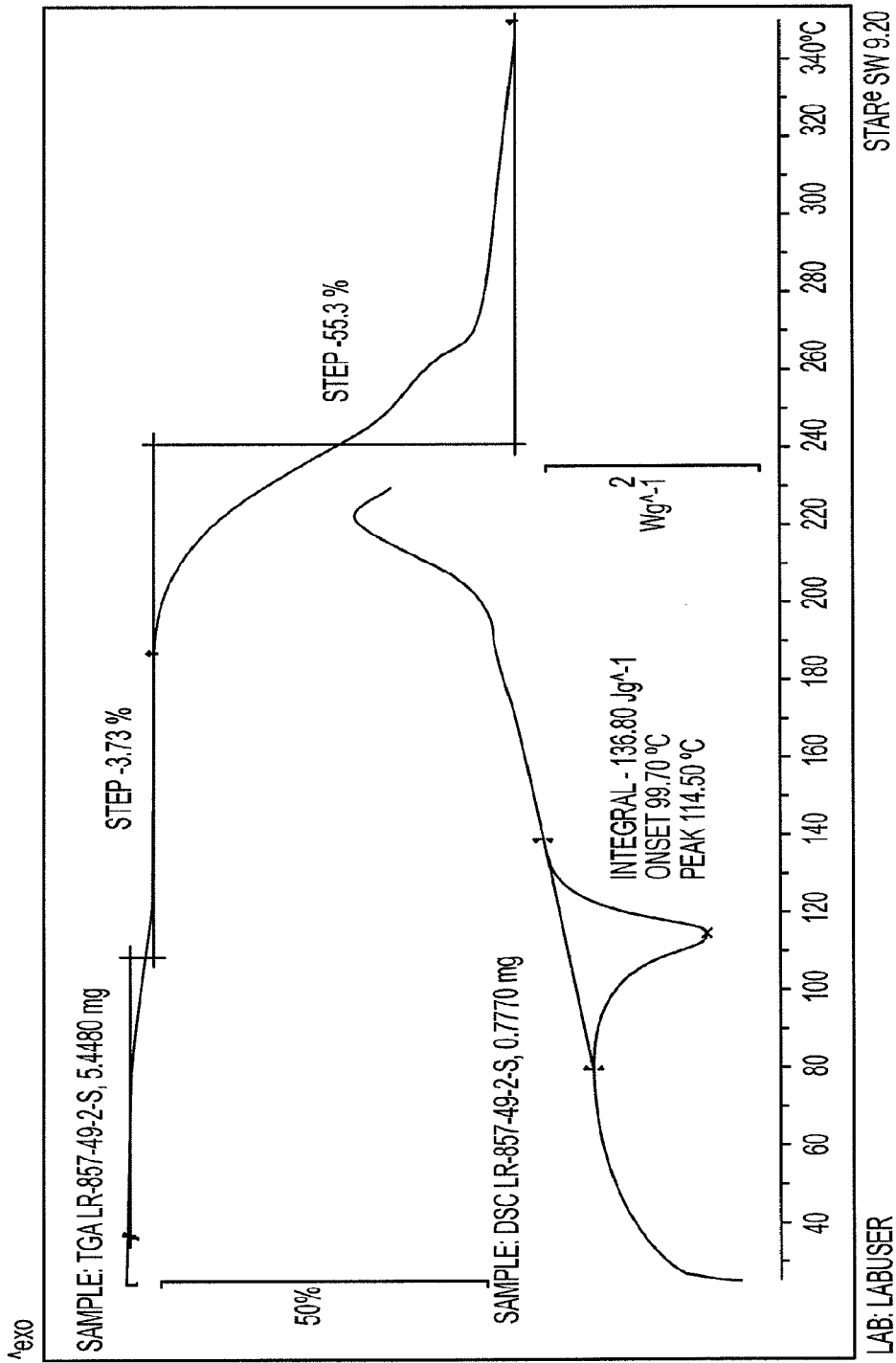
FIG. 9 shows the TGA and DSC profiles of Crystalline Form 1 of compound (V).

In one embodiment, Form 1 is characterized by a single endothermic transition at 99.7° C.±0.5° C. in the differential scanning calorimetry (DSC) profile shown in FIG. 9. The profile plots the heat flow as a function of temperature. The DSC is performed on the sample using a scanning rate of 10° C./min from 25° C. to 240° C.

Crystalline Form 1 can also be characterized by the thermal gravimetric analysis (TGA) profile shown in FIG. 9. The profile graphs the weight loss percentage of the sample as a function of temperature with the temperature rate change being 10° C./min from ambient temperature to 350° C. The profile shows a weight loss of approximately 3.7% as the temperature of the sample changed from 40° C. to 200° C., which indicates Form 1 is a monohydrate.

Figure 10:
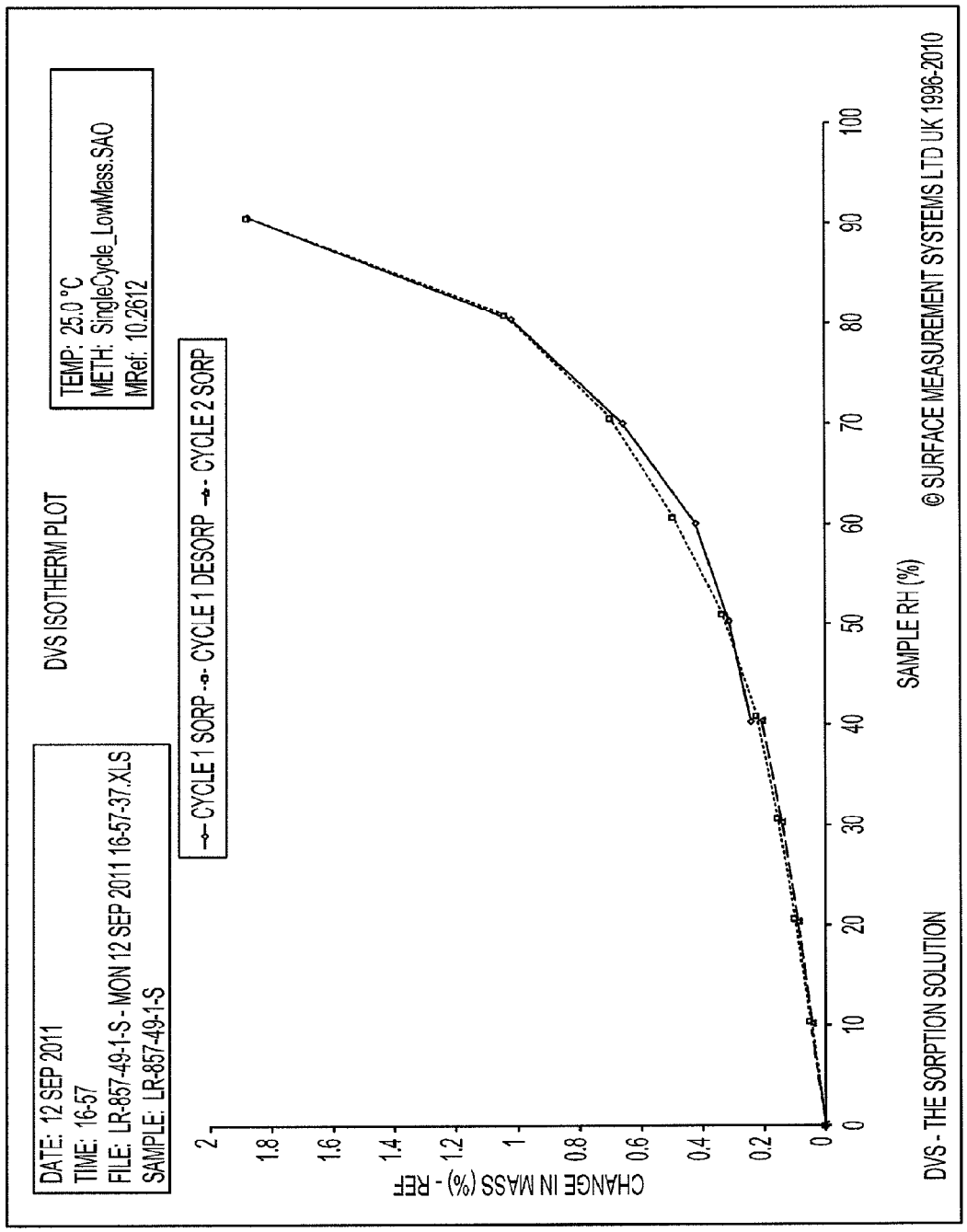
FIG. 10 shows GSV profile of Crystalline Form 1 of the compound (V).

Form 1 is also characterized by gravitational vapor sorption (GVS) profile shown in FIG. 10. The profile shows the change in weight of a sample as the relative humidity (RH) of the environment is changed between 0% and 90% at a 10% RH interval at 25° C. The adsorption profile shows a very small amount (1.6%) of weight gain between 40% RH and 90% RH. The desorption profile shows 1.9% weight loss between 90% RH and 0% RH, indicating no dehydration had occurred.

In one embodiment, Form 1 can be obtained by crystallization of the compound of formula (V) in a mixture of an organic solvent and water. Suitable organic solvents are as described above. In a particular embodiment, a mixture of acetone and water is used for crystallization. The volume ratio of acetone and water can be in the range of 80:20 to 99:1. Preferably, the ratio is 95:5. Crystallization can be carried out in a reduced temperature, preferably at −20° C.

Crystalline Form 2a

In one embodiment, at least a particular percentage by weight of the compound of formula (V) is Crystalline Form 2a of the compound. Particular weight percentages include 70%, 72%, 75%, 77%, 80%, 82%, 85%, 87%, 88%, 89%, 90%, 91%, 92%, 93%, 94%, 95%, 96%, 97%, 98%, 99%, 99.5%, 99.9%, 100% or a percentage between 70% and 100%.

Figure 11:
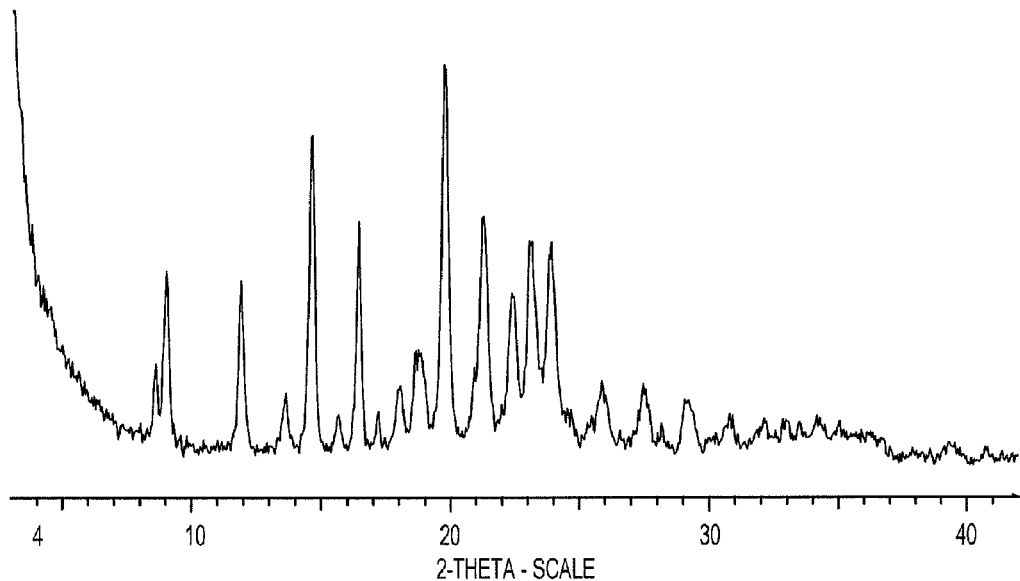
FIG. 11 shows the X-ray powder diffraction pattern of Crystalline Form 2a of compound (V).

Crystalline Form 2a is characterized by the X-ray powder diffraction (XRPD) pattern shown in FIG. 11 with values of 2θ angle and relative intensities as listed in Table 2, obtained using Cu Kα radiation. In a particular embodiment, Form 2a is characterized by one, two, three, four or five major XRPD peaks at 2θ angles of 8.6, 11.9, 16.5 and 24. In another particular embodiment, Form 2a is characterized by major XRPD peaks at 2θ angles of 11.9, 16.4 and 24.

TABLE 2

Characteristic peaks of Form 2a

| 2θ angle (°) | Intensity % |
|---|---|
| 8.6 | 30.8 |
| 9 | 52 |
| 11.9 | 50.3 |
| 13.6 | 24.1 |
| 14.6 | 83.5 |
| 15.7 | 19.5 |
| 16.5 | 64.2 |
| 17.2 | 21.1 |
| 18 | 26 |
| 18.6 | 34.3 |

TABLE 2-continued

Characteristic peaks of Form 2a

| 2θ angle (°) | Intensity % |
| --- | --- |
| 18.9 | 33.5 |
| 19.8 | 100 |
| 20.9 | 30.3 |
| 21.3 | 65 |
| 22.4 | 47.8 |
| 23.2 | 59.1 |
| 24 | 59.1 |
| 25.9 | 27.3 |
| 27.5 | 25.8 |
| 29.2 | 23.2 |
| 30.8 | 19.6 |

Figure 12:
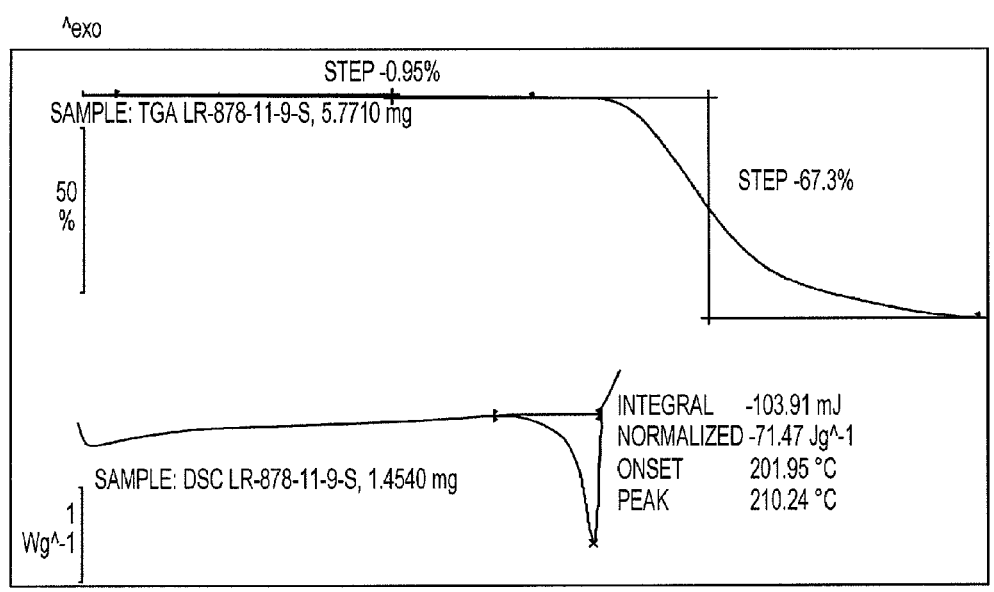
FIG. 12 shows the TGA and DSC profiles of Crystalline Form 2a of compound (V).

In one embodiment, Form 2a is characterized by a single endothermic transition at 201.9° C.±0.5° C. in the differential scanning calorimetry (DSC) profile shown in FIG. 121. Form 2a can also be characterized by the thermal gravimetric analysis (TGA) profile shown in FIG. 12. The profile shows a weight loss of approximately 0.9% as the temperature of the sample changed from 40° C. to 90° C., which indicates Form 2a is anhydrous.

Figure 13:
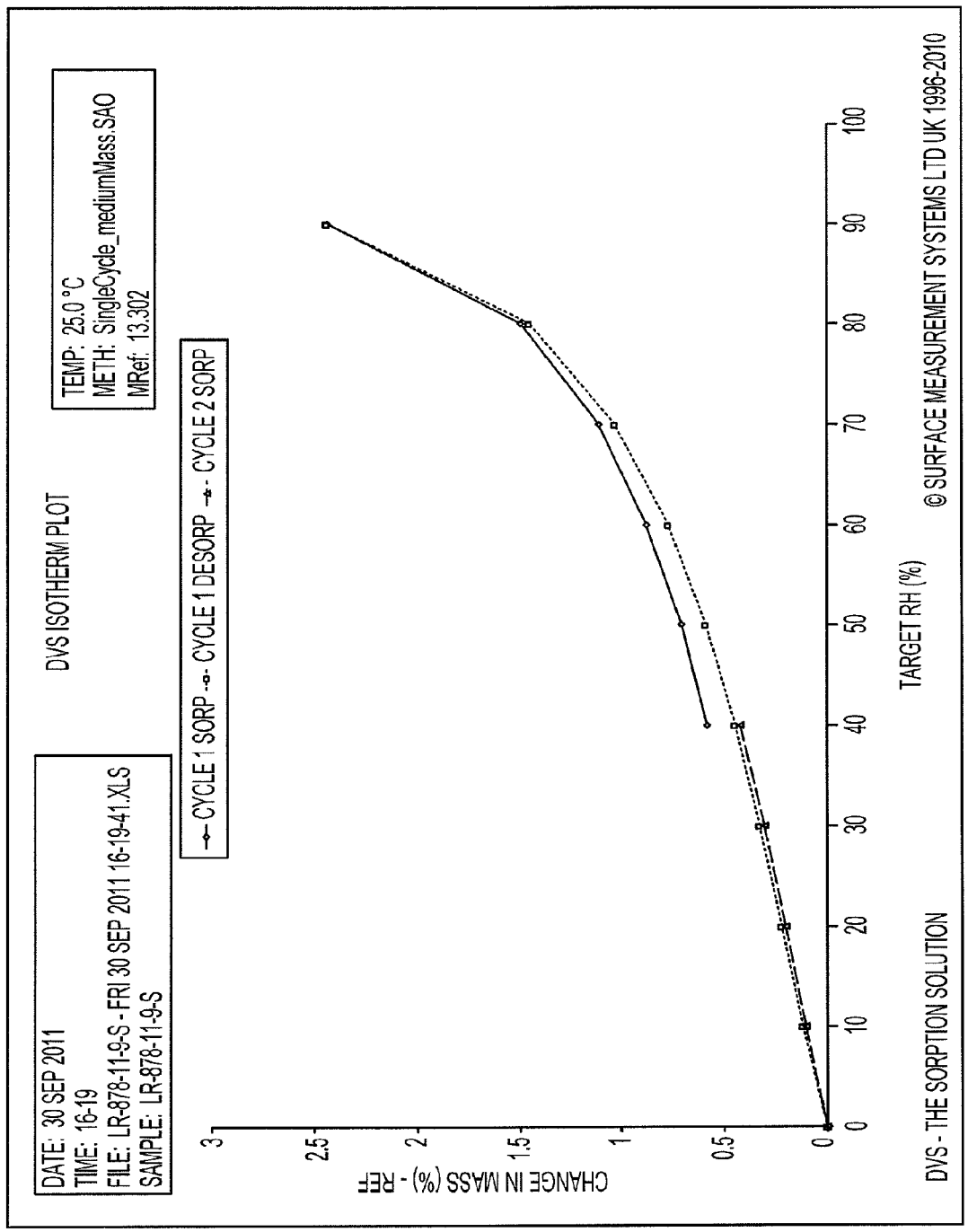
FIG. 13 shows GSV profile of Crystalline Form 2a of the compound (V).

Form 2a is also characterized by gravitational vapor sorption (GVS) profile shown in FIG. 13. The adsorption profile shows a very small amount (1.8%) of weight gain between 40% RH and 90% RH, indicating no hydration had occurred. The desorption profile shows 2.4% weight loss between 90% RH and 0 % RH.

In one embodiment, Form 2a can be prepared by crystallization of compound (V) in hydrophilic solvent or solvents as described above. In a particular embodiment, Form 2a is prepared by crystallization in acetone at a reduced temperature, such as −20° C.

In another embodiment, Form 2a can be prepared by removing the salt cation from a salt of compound (V), such as a DIPEA salt, by passing the salt through a cation exchange column or by adding an acid. Subsequent crystallization in a hydrophilic solvent, such as acetone or acetonitrile, gives Form 2a.

Crystalline Form 3

In one embodiment, at least a particular percentage by weight of the compound of formula (V) is crystalline form 3 of the compound. Particular weight percentages include 70%, 72%, 75%, 77%, 80%, 82%, 85%, 87%, 88%, 89%, 90%, 91%, 92%, 93%, 94%, 95%, 96%, 97%, 98%, 99%, 99.5%, 99.9%, 100% or a percentage between 70% and 100%.

Figure 14:
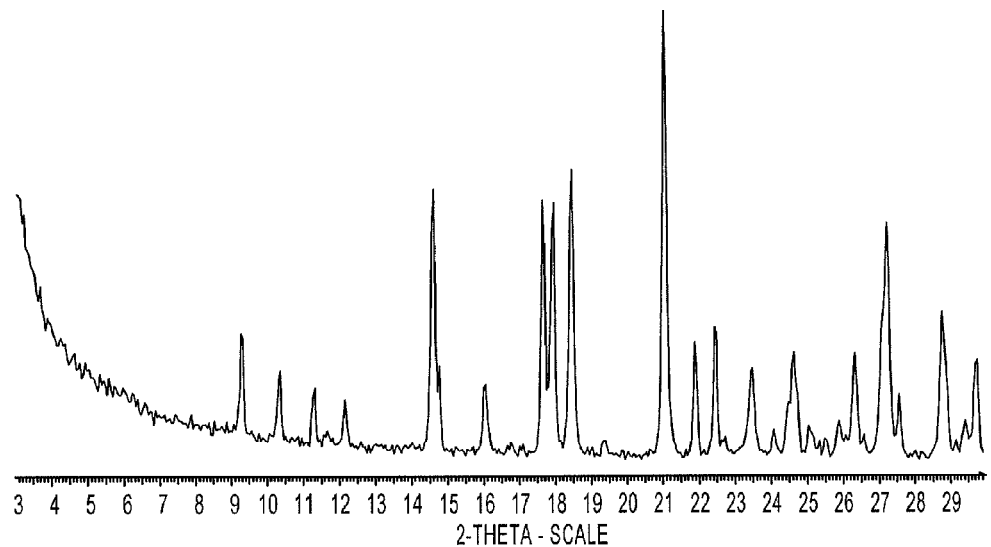
FIG. 14 shows the X-ray powder diffraction pattern of Crystalline Form 3 of compound (V).

Crystalline Form 3 is characterized by the X-ray powder diffraction (XRPD) pattern shown in FIG. 14 with values of 2θ angle and relative intensities as listed in Table 3, obtained using Cu Kα radiation. In a particular embodiment, Form 3 is characterized by one, two, three, four, five, six, seven, eight, nine or ten major XRPD peaks at 2θ angles of 10.4, 11.3, 12.2, 14.7, 17.6, 22.5, 26.3, 27.2, 28.8 and 29.8°. In another particular embodiment, Form 3 is characterized by major XRPD peaks at 2θ angles of 10.4, 1.3, 12.2, 17.6, 22.5, 26.3, 27.2 and 28.8°.

TABLE 3

Characteristic peaks of Form 3

| 2θ angle (°) | Intensity % |
| --- | --- |
| 9.3 | 30.8 |
| 10.4 | 23 |
| 11.3 | 19.6 |
| 12.2 | 16.8 |
| 14.6 | 61.9 |
| 14.7 | 24 |
| 16 | 19.8 |
| 17.6 | 59.6 |
| 17.9 | 58.7 |
| 18.4 | 66.1 |
| 21 | 100 |
| 21.9 | 29.8 |
| 22.5 | 32.6 |
| 23.5 | 24.1 |
| 24.5 | 16.4 |
| 24.6 | 26.9 |
| 26.3 | 27.1 |
| 27.2 | 54.6 |
| 27.6 | 18.2 |
| 28.8 | 35.4 |
| 29.8 | 25.3 |

Figure 15:
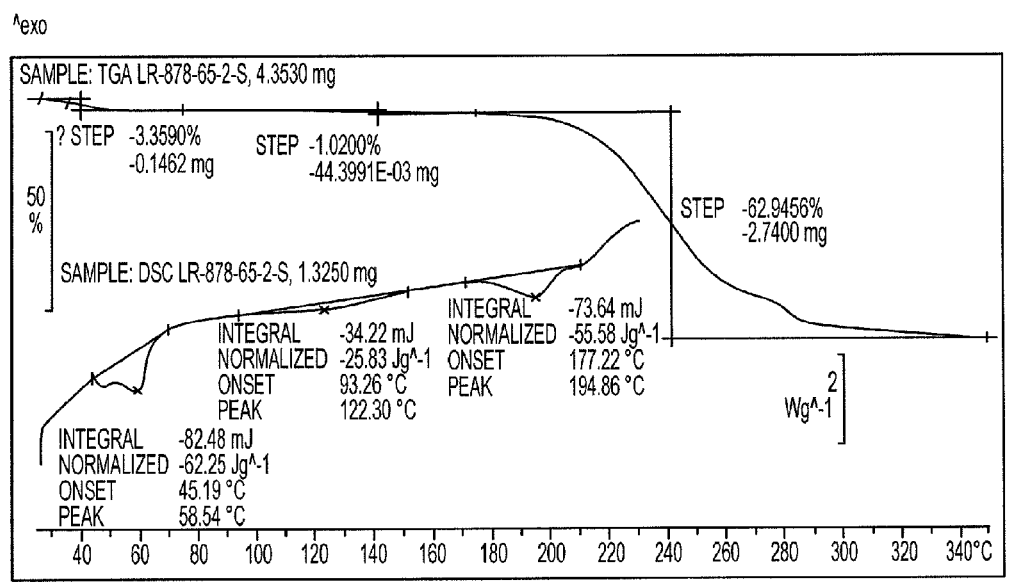
FIG. 15 shows the TGA and DSC profiles of Crystalline Form 3 of compound (V).

In one embodiment, Form 3 is characterized by endothermic transitions at 45.2±0.5° C., 93.3±0.5° C., and 177.2±0.5° C. in the differential scanning calorimetry (DSC) profile shown in FIG. 15. Form 3 can also be characterized by the thermal gravimetric analysis (TGA) profiled shown in FIG. 15. The profile shows a weight loss of approximately 4.48% as the temperature of the sample changed from room temperature to 180° C., which indicates Form 3 is a monohydrate.

Figure 16:
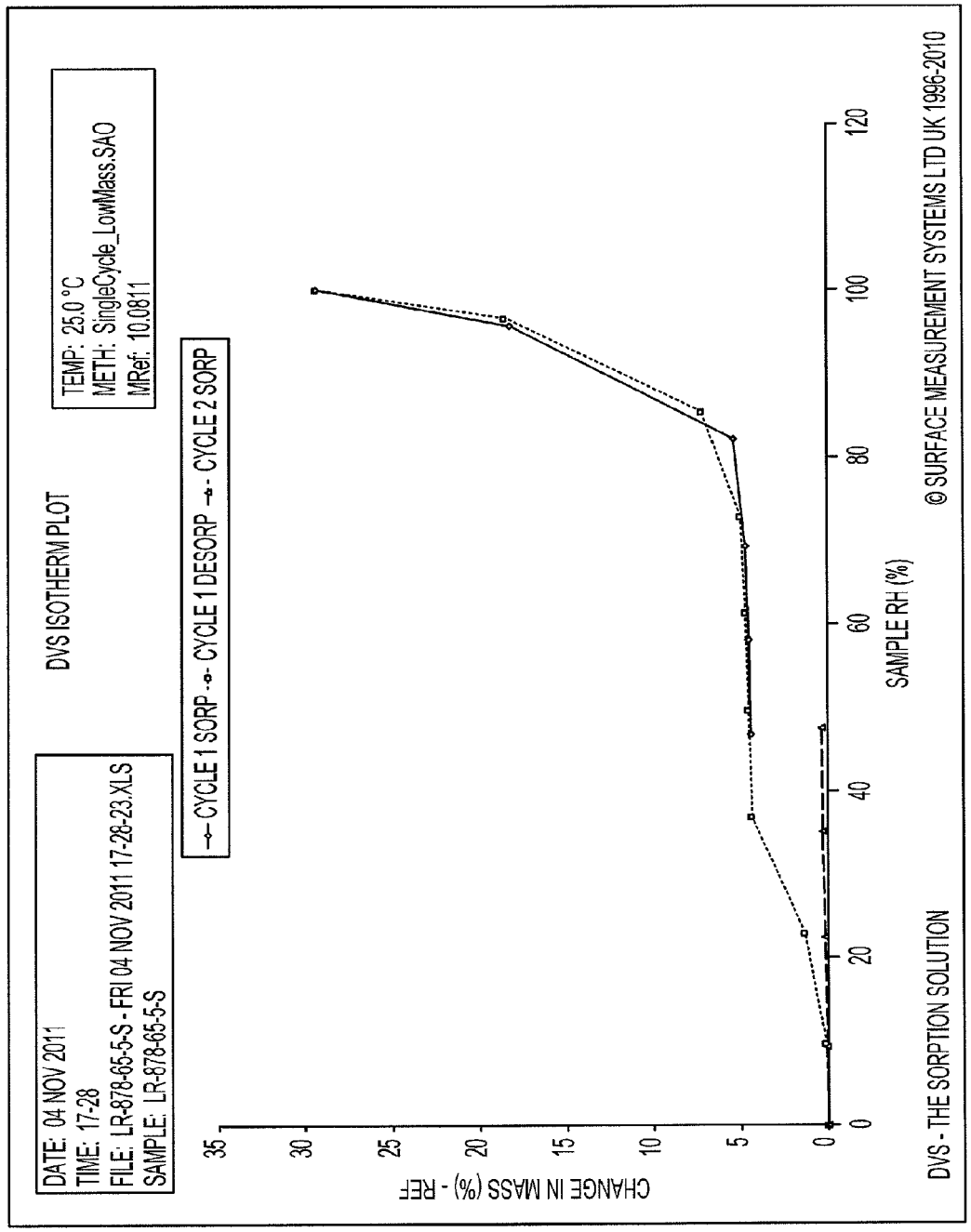
FIG. 16 shows GSV profile of Crystalline Form 3 of the compound (V).

Form 3 is also characterized by gravitational vapor sorption (GVS) profile shown in FIG. 16. The adsorption profile shows 25% of weight gain between 40% RH and 90% RH. The desorption profile shows 29.4% weight loss between 90% RH and 0 % RH. The second adsorption profile shows 0.4% weight gain between 0 % RH and 40% RH, indication dehydration had occurred during the desorption.

In one embodiment, Form 3 is prepared by crystallizing a salt (e.g., DIPEA salt) in a mixture of an organic solvent and water containing a small amount of an acid. Suitable organic solvents are as described above. In a particular embodiment, the organic solvent is acetone. Preferably, the volume ratio of acetone to water is about 80:20 to about 99:1. Even more preferably, the ratio is about 90:10 to about 95:10. Any suitable acids described herein can be used. In one embodiment, the acid is HCl or H2S04. An amount of about 0.1 to about 5 equivalent of the acid relative to the salt can be used. In a particular embodiment, about 0.1 to about 1.5 equivalent of the acid, preferably about 0.5 to about 1.0 equivalent of the acid can be used. Crystallization can be carried out in a reduced temperature described herein, for example at about −20° C.

Crystalline Form 2b

In one embodiment, Crystalline Form 3 can be converted to an anhydrous crystalline form, Crystalline Form 2b, by dehydration or drying under vacuum. In one embodiment, dehydration is carried out at 0% RH using $P_2O_5$ as dessicant. In another embodiment, Crystalline Form 2b can be prepared by drying Crystalline Form 3 under vacuum at 30° C. for 24 hours.

Figure 17:
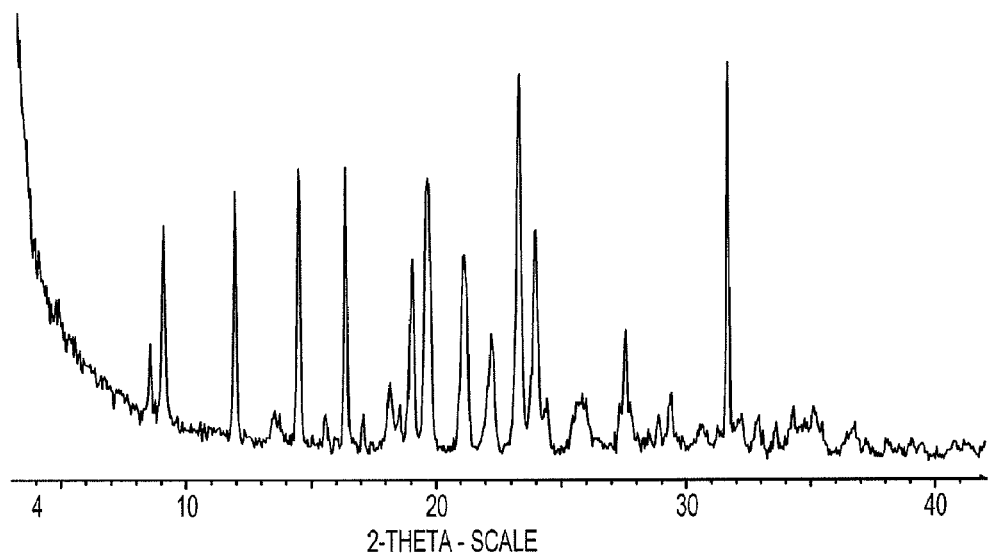
FIG. 17 shows the the X-ray powder diffraction pattern of Crystalline Form 2b of compound (V).

Crystalline Form 2b is characterized by the X-ray powder diffraction (XRPD) pattern shown in FIG. 17 with values of 2θ angle and relative intensities as listed in Table 4, obtained using Cu Kα radiation. In a particular embodiment, Form 2b is characterized by one, two, three, four or five major XRPD peaks at 2θ angles of 8.5, 11.9, 16.4, 24 and 31.7 0. In another embodiment, Form 2b is characterized by a major XRPD peak at 2θ angles of 31.7° and one, two, three or four major XRPD peaks at 2θ angles of 8.5, 11.9, 16.4 and 24 0. In another particular embodiment, Form 2b is characterized by major XRPD peaks at 2θ angles of 11.9, 16.4, 24 and 31.7°.

TABLE 4

Characteristic peaks of Form 2b

| 2θ angle (°) | Intensity % |
|---|---|
| 8.5 | 33.2 |
| 9.1 | 61.8 |
| 11.9 | 70 |
| 13.5 | 17.4 |
| 14.4 | 74.6 |
| 15.5 | 16.3 |
| 16.4 | 74.9 |
| 17.1 | 15.7 |
| 18.1 | 24 |
| 18.5 | 18.2 |
| 19.1 | 53.2 |
| 19.6 | 72.3 |
| 21.1 | 54.6 |
| 22.2 | 35.2 |
| 23.3 | 97.7 |
| 24 | 60.3 |
| 25.8 | 21.4 |
| 27.6 | 36.6 |
| 29.3 | 21.4 |
| 30.6 | 13.8 |
| 31.7 | 100 |

A fifth embodiment of the invention discloses alternate methods of preparing compounds of the formula (III), wherein Q represents a disulfide moiety, or (IV). This embodiment provides a process for the preparation of compounds of formula (3) or (IV) comprising:

a) reacting a lactone of formula (4) with a sulfonating agent to form a compound of formula (5) or a salt thereof. Preferably, the sulfonating agent is chlorosulfonic acid or sulfur trioxide in its free or complexed form, such as a complex with dimethylformamide, or an amine exemplified by pyridine or triethyl amine. Preferably, the sulfonating agent is sulfur trioxide in its free form.

b) reacting the compound of formula (5) or a salt thereof with a sulfur-bearing nucleophile, optionally in the presence of a base and/or an acid or Lewis acid (Fujita et al., 1978 Tetrahedron Letters, 52, 5211; Kelly et. Al. 1977, Tetrahedron Letters, 49, 3859). Preferably, the sulfur-containing nucleophile is selected from hydrogen sulfide, or a salt thereof, thiourea, thioacetic acid, 2-(trimethylsilyl) ethanethiol or thiophenol. More preferably, the sulfur-containing nucleophile is thiourea, thioacetic acid or thiophenol. Any suitable bases, acids or Lewis acids known in the art can be used in the present methods. Preferably the base is selected from n-butyl lithium, lithium diisopropylamine, diisopropyl ethyl amine or triethyl amine. More preferably, the base is n-butyl lithium. The base, if used, in these cases can be premixed with the thiol-bearing nucleophile then reacted with a compound of formula (5). Alternatively, the base, if used, can be added to a mixture of a compound of formula (5) and the thiol-bearing nucleophile. Preferably the base is premixed with the thiol-bearing nucleophile then reacted with a compound of formula (5). Preferably, the acid or Lewis acid, if used, is selected from 4-toluene sulfonic acid, aluminum trichloride, boron trifluoride, or titanium tetrachloride. More preferably, the acid or Lewis acid if used is 4-toluene sulfonic acid or aluminum trichloride. Typically such reactions are conducted at ambient temperature in solvents such as dichloromethane, or 1,2-dichloroethane when a strong base is not employed. When a strong base is used reactions are typically done at between −40 to 25° C.

c) Optional deprotection to release the free thiol. The deprotection can be carried out by several means. Thioesters or thiouronium salts can be hydrolyzed with bases such as NaOH or Na$_2$CO$_3$, (Zervas et. Al. 1963, J. Am. Chem. Soc. 85, 1337). Trimethylsilyl ethanol esters can also be deprotected using fluoride containing agents such as hydrogen fluoride, or tetrabutylammonium fluoride (Hamm et. Al. 2004, Org. Lett. 6, 3817) and thiophenol adducts can be deprotected by electrolysis or by palladium acetate (Chung et al, 2004, J. Chem. Soc. 126, 7386). Preferably, the deprotection involves hydrolysis with a base, such as NaOH or KOH. Typically such reactions are conducted in an aqueous NaOH or KOH solution, optionally mixed with a water-miscible solvent, such as methanol, ethanol, THF, and at ambient temperature.

d) reacting the compound of formula (6) or a salt thereof with a mixed disulfide compound to provide the compound of formula (3) or (IV). Preferably, the mixed disulfide compound is selected from 2,2'-dithiodipyridine, 4,4'-dithiodipyridine, 2,2'-dithiobis(5-pyridine), 4 nitrophenyldisulfide, S-methyl methanethiosulfonate or dimethyl disulfide. More preferably, the mixed disulfide compound is 2,2'-dithiodipyridine. Other suitable disulfide compounds are known in the art (see Aslam and Dent, 2000, Bioconjugation: Protein coupling techniques for the biomedical sciences, MacMillan, London)

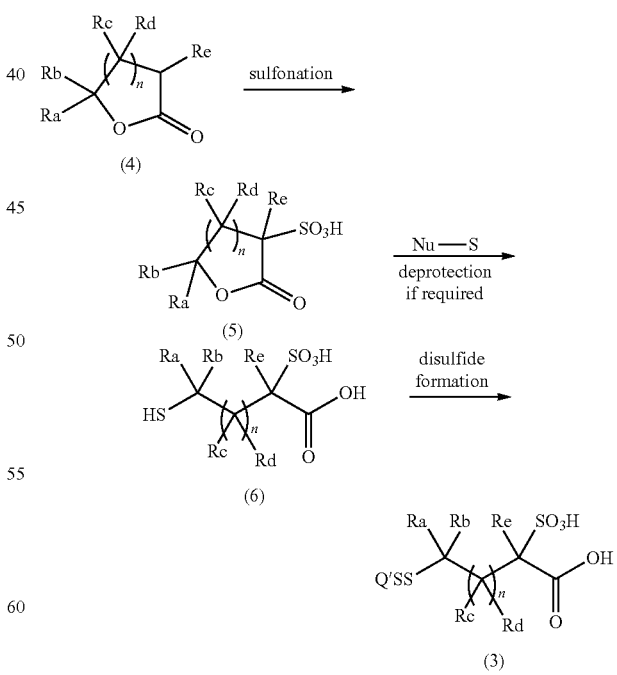

n = 0, 1, 2, 3 or 4

Q' is a linear, branched or cyclic alkyl having 1 to 10 carbon atoms, phenyl, ortho or para-nitrophenyl, dinitrophenyl, pyridyl or nitropyridyl; $R_a$, $R_b$, $R_c$, $R_d$ and $R_e$, each independently, is H or a linear, branched or cyclic alkyl having 1 to 10 carbon atoms. Preferably, $R_a$, $R_b$, $R_c$, $R_d$ and $R_e$, each independently, is H or a linear or branched alkyl having 1 to 4 carbon atoms. More preferably, $R_a$, $R_b$, $R_c$, $R_d$ and $R_e$ are all H.

A more direct method of preparing (3) or (IV) would be the alpha sulfonation of a thiolactone followed by hydrolysis of the resulting product and reaction with a disulfide forming agent.

A sixth embodiment provides a process for the preparation of compounds of formula (3) or (IV) comprising:

a) reacting a thiolactone of formula (7) with a sulfonating agent to form a compound of formula (8) or a salt thereof; Preferably, the sulfonating agent is chlorosulfonic acid or sulfur trioxide in its free or complexed form, such as a complex with dimethylformamide, or an amine exemplified by pyridine or triethyl amine. Preferably, the sulfonating agent is sulfur trioxide in its free form;

b) hydrolyzing the compound of formula (8) or a salt thereof to form a compound of formula (6) or a salt thereof. Preferably, the hydrolysis is carried out in the presence of NaOH or KOH.

c) reacting the compound of formula (6) or a salt thereof with a disulfide compound to provide the compound of formula (3) or a salt thereof. Preferably, the disulfide compound is selected from 2,2'-dithiodipyridine, 4,4'-dithiodipyridine, 2,2'dithiobis(5-pyridine), 4 nitrophenyldisulfide, S-methyl methanethiosulfonate or dimethyl disulfide. More preferably, the disulfide compound is 2,2'-dithiodipyridine,

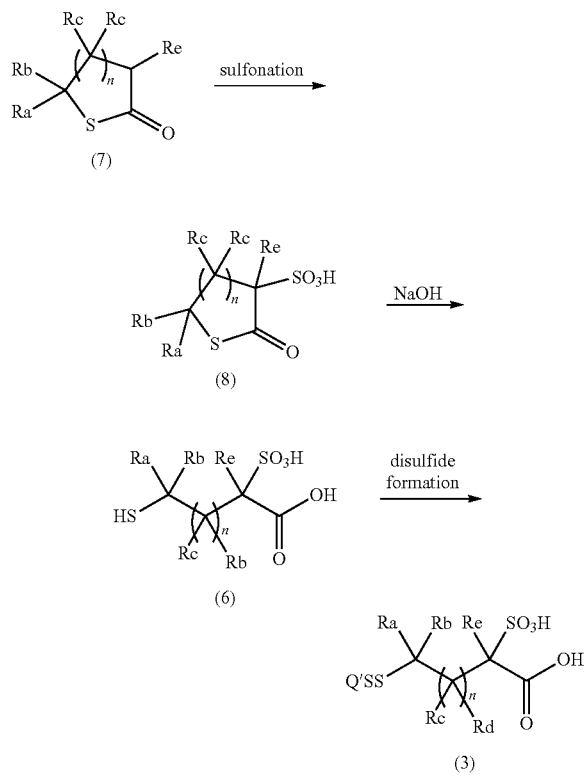

n = 0, 1, 2, 3 or 4

Q' is a linear, branched or cyclic alkyl having 1 to 10 carbon atoms, phenyl, ortho or para-nitrophenyl, dinitrophenyl, pyridyl or nitropyridyl; $R_a$, $R_b$, $R_c$, $R_d$ and $R_e$, each independently, is H or a linear, branched or cyclic alkyl having 1 to 10 carbon atoms. Preferably, $R_a$, $R_b$, $R_c$, $R_d$ and $R_e$, each independently, is H or a linear or branched alkyl having 1 to 4 carbon atoms. More preferably, $R_a$, $R_b$, $R_c$, $R_d$ and $R_e$ are all H.

In one embodiment, the compound of formula (3) prepared according the processes described in the fifth and sixth embodiments can react with a hydroxy or mercapto compound to form a compound of formula (Ia):

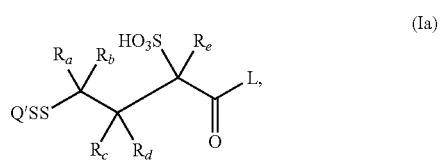

(Ia)

or a salt thereof, wherein $R_a$, $R_b$, $R_c$, $R_d$, $R_e$, L and Q' are as described above.

Salts of the compounds of the present invention containing a carboxylic acid and/or sulfonic acid or other acidic functional group can be prepared by reacting the compounds with a suitable base. Suitable base includes, but is not limited to, alkali metal salts (especially sodium and potassium), alkaline earth metal salts (especially calcium and magnesium), aluminum salts and ammonium salts, tetraalkyl ammonium salts (such as tetramethyl ammonium, tetraethylammonium) as well as salts made from organic bases such as trimethylamine, triethylamine, and pyridine. Preferably, the salts are $Na^+$ or $K^+$ salts.

Particularly, the sulfonic acid moiety in the compounds described herein (e.g., compound of formula (I), (III) and (V)), can exist as a free acid or a salt thereof. Preferably a given batch of the compound would exist substantially as a free acid or in a single salt form such as $Na^+$, $K^+$, $NMe_4^+$ or the like. Such conversions can be conducted by several means including but not limited to the following. A compound of formula (I), (III) or (V) can be brought into a solution or suspension with a buffer or buffer/solvent mixture containing the counter ion of interest in order to exchange the ions. After which the desired compound or a salt bearing the cation of interest (J) can be purified from the mixture in several ways. Preferably, any water and solvent are evaporated and the desired compound is dissolved in an organic solvent then filtered to remove any inorganic salts. Such filtration can be done through an ordinary filter of through a relatively small amount of a filter aid such as but not limited to diatomaceous earth, silica, or alumina. Alternatively a solution of compound of formula (I), (III) or (V) is eluted through cation exchange material which has been conditioned with the cation of interest. Alternatively a solution of the compound can be mixed in a "batch mode" with cation exchange material that has been conditioned with the cation of interest to complete exchange then ion exchange material can be removed by filtration. Alternatively a solution of the compound can be captured on anion exchange material then released by eluting in batch or chromatographic mode with solvent containing the desired cation. Capturing by anion exchange chromatography followed by displacement with a cation of interest is most advantageous when the cation is volatile such as triethyl amine or diisopropyl ethyl amine. Examples of ion exchange materials which are appropriate for this application are well known to one skilled in the art and include, Dowex resins, such as Dowex 1, Dowex 50, DEAE resins or Amberlite resins The invention also encompasses methods for freezing a solution of compounds of formula (I), (III) or (V) and removing the frozen solvent by lyophilization, also known as freeze drying. Solvents or mixtures of solvents that are suitable for this application should be able to dissolve compounds of formula (I), (III) or (V) and the solvent or solvents should be volatile under the vacuum conditions employed in the lyophilization process. The solvent or solvent system should also remain frozen during the lyophilization process. Such solvents or solvent systems include but are not limited to water, 1,4-dioxane, tert-butanol, solutions of water and acetonitrile, solutions of water and methanol, solutions of 1-4-dioxate and tert-butanol. Each of these single solvents or mixtures of solvents can also contain an acidic or basic additive that is volatile under the lyophilization conditions. Acidic or basic additives that are suitable for this application include but are not limited to formic acid, acetic acid, trifluoroacetic acid, triethylamine, or diisopropyl ethyl amine.

Schemes for the synthesis of compounds using the processes disclosed in the present invention are shown in FIGS. 4-7. FIG. 4 shows the synthesis of N-succinimidyl 4-(2'-pyridyldithio)-2-sulfobutanoate (sulfo-SPDB). 4-(2-pyridyldithio)butanoic acid was prepared as previously described (Widdison et al., 2006, *J. Med. Chem.*, 49, 4392-44080. Direct sulfonation with chlorosulfonic acid in the presence of diisopropylethyl amine (DIPEA) resulted in sulfonation at the C2 position to provide 4-(2'-pyridyldithio)-2-sulfobutanoic acid. Reaction with N-hydroxysuccinimide (NHS) in the presence of EDC provided the desired sulfo-SPDB crosslinker.

This direct sulfonation reaction can be utilized to produce a number of α-sulfocarboxylic acids from carboxylic acids. Examples of the synthesis of a variety of such compounds from commercially available carboxylic acids are shown in FIGS. 5-7. These carboxylic acid compounds contain a thiol reactive group, such a disulfide (FIG. 5), a maleimide (FIG. 6), haloacetyl or a haloacetamido (FIG. 7) to enable reaction with a thiol-containing agent. The resulting sulfo-carboxylic acids can be converted to active esters using a hydroxyl of mercapto compound in the presence of a coupling agent, such as EDC, in an analogous manner to sulfo-SPDB shown in FIG. 4 and in the Examples to provide the bifunctional crosslinking agent. The active ester moiety can react with a cell binding agent or a cytotoxic compound or label bearing an amino or hydroxyl group, while the disulfide, maleimide, haloacetyl or haloacetamido moiety can undergo reaction with a cell binding agent or a cytotoxic compound or a label bearing a thiol group, thus linking the cell binding agent with the cytotoxic compound or label.

DEFINITIONS

"Linear or branched alkyl" as used herein refers to a saturated linear or branched-chain monovalent hydrocarbon radical having one to twenty carbon atoms, preferably one to ten carbon atoms, more preferably one to four carbon atoms. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like.

"Linear or branched alkenyl" refers to linear or branched-chain monovalent hydrocarbon radical of two to twenty carbon atoms, preferably two to ten carbon atoms, more preferably two to four carbon atoms, with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

"Linear or branched alkynyl" refers to a linear or branched monovalent hydrocarbon radical of two to twenty carbon atoms, preferably two to ten carbon atoms, more preferably two to four carbon atoms, with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like.

The terms "cyclic alkyl", "cyclic alkenyl", "cyclic alkynyl", refer to a monovalent non-aromatic, saturated or partially unsaturated ring having 3 to 10 carbon atoms as a monocyclic ring or 7 to 10 carbon atoms as a bicyclic ring. Bicyclic carbocycles having 7 to 10 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-I-enyl, 1-cyclopent-2-enyl, 1-cyclopent-3-enyl, cyclohexyl, 1-cyclohex-I-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "cycloalkyl" refers to a monovalent saturated monocyclic ring radical having 3 to 10 carbon atoms. Preferably, the cycloalkyl has 3 to 7 carbon atoms in the ring. Examples of cycloalkyl include, not are not limited to cyclopropyl, cyclobutyl, cyclopentyl, cyclopentyl, cyclohexyl and cycloheptyl.

The term "alkyl" refers to linear, branched or cyclic alkyl described above.

The terms "heterocycloalkyl" are used interchangeably herein and refer to a saturated or a partially unsaturated (i.e., having one or more double and/or triple bonds within the ring) carbocyclic radical of 3 to 6 ring atoms in which at least one ring atom is a heteroatom selected from nitrogen, oxygen, phosphorus, and sulfur, the remaining ring atoms being C, where one or more ring atoms is optionally substituted independently with one or more substituents described below. Preferably, heterocycloalkyl is fully saturated. A heterocycloalkyl may be a monocycle having 3 to 6 ring members (1 to 3 carbon atoms and 1 to 3 heteroatoms selected from N, O, and S). Heterocycloalkyls are heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycloalkyls include, but are not limited to, aziridine, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl.

The term "heteroaromatic group" refers to a monovalent aromatic radical of 5 to 12 membered monocyclic or bicyclic rings, containing one or more heteroatoms independently selected from nitrogen, oxygen, and sulfur, wherein one or more ring atoms is optionally substituted independently with one or more substituents described below. Preferably, the heteroaromatic group is 5 or 6-membered monocyclic ring. Examples of heteroaromatic groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl.

By way of example and not limitation, nitrogen bonded heterocycloalkyls or heteroaromatics are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaromatic groups or heterocycloalkyls include the oxidized forms such as NO, SO, and $SO_2$.

Unless otherwise indicated, the cyclic, branched or cyclic alkyl, alkenyl or alkynyl, cycloalkyl, heterocycloalkyl, phenyl, heteroaromatic group described herein can be optionally substituted. Suitable substituents include, but are not limited to, halogen, —OH, alkyl, alkoxy, haloalkyl, alkoxyalkyl, —$NH_2$, alkylamino, dialkylamino, wherein the alkyl group in the substituent groups is unsubstituted linear or branched alkyl having 1 to 4 carbon atoms. The heteroaromatic group and phenyl group can also be substituted with —CN and/or —$NO_2$ groups.

The term "alkoxy" refers to an alkyl radical attached through an oxygen linking atom. "Alkoxy" can also be depicted as —O-alkyl. Preferably, the alkyl radical attached to the oxygen linking atom has 1 to 10 carbon atoms, preferably 1 to 4 carbon atoms. Examples of alkoxy include, but are not limited to, methoxy, ethoxy, propoxy, and butoxy.

The term "haloalkyl" refers to an alkyl radical substituted with one or more (e.g., two, three, four, five or six) halogen groups. Preferably, the haloalkyl group has 1 to 10 carbon atoms, preferably 1 to 4 carbon atoms.

The term "alkylamino" refers to an alkyl radical attached through a —NH linking group. "Alkylamino" can also be depicted as —NH-alkyl. Preferably, the alkylamino group has 1 to 10 carbon atoms, preferably 1 to 4 carbon atoms.

The term "dialkylamino" refers to a group depicted as —N(alkyl)(alkyl). Preferably, each alkyl depicted in —N(alkyl)(alkyl) has 1 to 10 carbon atoms, preferably 1 to 4 carbon atoms.

The term "halo" or "halogen" refers to F, Cl, Br or I.

The term peptide is intended to include moieties comprising two or more sequentially linked amino acids selected from natural or unnatural amino acids, including modified amino acids, such as, but not limited to, N-alkyl, N-aryl. Each of the said amino acids can be of the L-configuration, the D-configuration or racemic.

The term "amino acid residue" refers to an amino acid with the hydrogen atoms removed from the terminal carboxy and amino groups, i.e., —NHCH(R)C(=O)O—, R is the side chain group.

The term "sulfonating agent" refers to an agent that can introduce a sulfonic acid moiety in a compound. Sulfonating agents that may be used in methods described herein are known in the art (see U.S. Pat. No. 1,926,422; W. Thaler 1953, *Macromolecules* 16; 623-628; Truce and Olson, 1953, *J. Am. Chem. Soc.*, 75, 1651-1653) and include sulfur trioxide in its free or complexed form, such as complexed with dimethylformamide or dimethylacetamide, complexed with an amine, such as pyridine or triethylamine. The sulfonating agent can also be a halosulfonic acid, such as chlorosulfonic acid and fluorosulfonic acid. Alkylsulfates, acid sulfites, sulfites and sulfuryl chloride may also be used (Kharasch and Read 1939, *J. Am. Chem. Soc.*, 61, 3089-3092). There is also a report suggesting that lactones can undergo alpha-sulfonation with sulfur trioxide (Patent DE 800410). The sulfonation reaction described herein can be performed in solvents such as 1,4-dioxane, THF, ether or poly-ether, acetonitrile, DMF, and halogenated solvents, Preferably the sulfonation reaction is performed in halogenated solvents such as dichloromethane, chloroform and 1,2-dichloroethane, more preferably in 1,2-dichloroethane. Though sulfonation using chlorosulfonic acid is preferred to be performed in a halogenated solvent, it can also be performed in neat chlorosulfonic acid. Typically, the sulfonation is conducted at between 25-110° C. when chlorosulfonic acid is used as the sulfonating agent. Preferably, the sulfonation is conducted at between 50-100° C., and more preferably between 70-90° C. When sulfur trioxide is used as the sulfonating agent reactions are typically conducted at −40 to 25° C., preferably −20 to 5° C.

The term "coupling reagent" refers to a reagent that activates carboxylic acid group towards amide and ester formation. Coupling reagents that can be used in the processes described herein are known in the art. Examples of coupling reagents include, but are not limited to, N,N'-dicyclohexylcarbodiimide (DCC), 1-ethyl-3-(3-dimethylaminopropyl) carbodiimide (EDC), N,N'-diisopropyl carbodiimide (DIC), 1-ethoxycarbonyl-2-ethoxy-1,2-dihydroquinoline (EEDQ). Typically these couplings are done at ambient temperature in an aprotic solvent, several suitable solvents that are typically employed are dichloromethane, tetrahydrofuran and dimethyl formamide. Coupling methods and conditions are well known in the art (see Benoiton, 2006, Chemistry of Peptide Synthesis, CRC Press, Florida)

The term "a thiol reactive group" represents a group that can react with a thiol group in a thiol-containing compound. For example, a thiol reactive group can be a disulfide group or a maleimide, haloacetyl or a haloacetamido, vinylsulfones, vinylsulfonamides, vinylpyridines, oxiranes or aziridines.

The term "amine or hydroxyl-reactive group" represents a reactive ester or thioester group that contains a leaving group that is readily displaced by an amine group or a hydroxyl group. Reactive ester or thioester groups are known in the art. For example, a reactive ester can be an N-hydroxysuccinimide ester, N-hydroxy sulfosuccinimide ester, phthalimidyl ester, nitrophenyl ester, tetrafluoro phenyl ester, pentafluorophenyl ester, a thiopyridyl ester a thionitrophenyl ester. Other amine and hydroxyl-reactive groups are known in the art (see Aslam and Dent, 2000, Bioconjugation: Protein coupling techniques for the biomedical sciences, MacMillan, London).

The term "sulfur-bearing nucleophile" refers to compounds bearing a sulfur atom in which the sulfur atom can displace a leaving group or cause ring-opening on a separate compound. In the case of a lactone, sulfur nucleophile attack results in ring-opening to generate a carboxylic acid. Such reactions can be performed at room temperature or at elevated temperatures, such as 25 to 100° C. Such displacement reactions could occur in solution without additives or the displacement may require the aid of an acid, Lewis acid or a base. Examples of suitable sulfur nucleophiles include hydrogen sulfide, sodium hydrosulfide, thiourea and thioacetic acid. Other examples and appropriate reaction conditions are known to one skilled in the art (see Cremlyn, 1996, *An introduction to organosulfur chemistry*, Wiley, New York; Jerry March & Michael B. Smith, 2007 March's *Advanced Organic Chemistry*, Wiley, New York).

The term "salt" refers to a salt prepared from a compound of the present invention having an acidic functional group, such as a carboxylic acid or a sulfonic acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkyl amines; dicyclohexylamine; tributyl amine; triethyl amine, diisopropylethyl amine (DIPEA) or tributyl amine, pyridine; 4-alkylmorpholine, such as 4-methylmorpholine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "salt" also refers to a salt prepared from a compound of the present invention having a basic functional group, such as an amine functional group, and a pharmaceutically acceptable inorganic or organic acid. Suitable acids include, but are not limited to, hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, $ClSO_3H$ can be referred to as "chlorosulfonic acid," "chlorosulfuric acid" or "sulfurochloridic acid" or other names that one skilled in the art would readily recognize as representing $ClSO_3H$.

Unless otherwise indicated, bases, acids or Lewis acids that can be used in the processes described above are any suitable bases known in the art. Examples of suitable bases include, but are not limited to, n-butyllithium, lithium diisopropylamine, diisopropylethylamine, triethylamine, tributylamine. Examples of suitable acids and Lewis acids include, but are not limited to, benzosulfonic acid, 4-toluenesulfonic acid, sulfuric acid, hydrobromide, trifluoroacetic acid, aluminum trichloride and titanium tetrachloride.

All patents, patent publications and non-patent literature cited herein are expressly incorporated by reference in their entireties.

EXAMPLES

Example 1

General Method for α-Sulfonation of Carboxylic Acids

To a stirred solution of the carboxylic acid compound acid in anhydrous 1,2-dichloroethane (~0.2 M) is added chlorosulfonic acid (5 equivalent) and the mixture is stirred in a 75° oil bath for 35 min. The heating bath is removed and the mixture allowed to cool to ambient temperature then poured onto ice. The mixture is brought to pH 10~11 by the addition of 10% NaOH and stirred for 10 min. Then the solution is adjusted to pH 5 with 5% HCl and the mixture is transferred into a separatory funnel. The organic layer is extracted with deionized water and the aqueous layers are combined, washed with dichloromethane and concentrated under vacuum until inorganic salts begin to appear on the wall of the flask. The remainder is diluted with $CH_3CN$ and two layers formed are transferred into a separatory funnel. The bottom light brownish layer is separated, diluted with a small amount of deionized water, $CH_3CN$ and formic acid ($H_2O/CH_3CN/HCOOH$, 10:1:1). It is loaded on a C18 column and purified (eluting with $CH_3CN/H_2O$: 2% $CH_3CN$, 0-5 minutes; 2% to 28% $CH_3CN$, 5-20 minutes; 28-90% $CH_3CN$, 20-20:30 minutes; 90% $CH_3CN$, 20:30-25:30 minutes; 90-2% $CH_3CN$, 25:30-26 min; 2% $CH_3CN$, 26-28 min) to give the desired sulfo-SPDB acid 3 as light brownish oil. The top $CH_3CN$ layer is concentrated under reduced pressure, diluted with H₂O and HCOOH (10:1), loaded on C18 column and eluted with CH₃CN/H₂O to give more of the sulfonated product acid.

Example 2

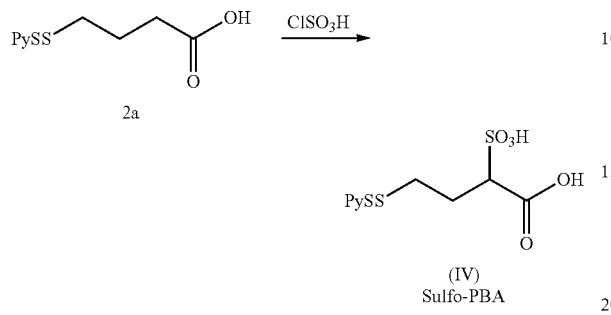

(IV)
Sulfo-PBA

Preparation of 4-(2'-pyridyldithio)-2-sulfo-butanoic acid (IV) without addition of base in the reaction To a stirred solution of 4-(2-pyridyldithio)butanoic acid (2a) (804 mg, 3.51 mmol) in anhydrous 1,2-dichloroethane (20 mL) was added chlorosulfonic acid (1.4 mL, 21 mmol) quickly via a syringe. The mixture was heated in a 75° C. oil bath and stirred at 73~78° C. for 27 min. The heating bath and the reaction mixture was allowed to cool to ambient temperature and then the reaction mixture was poured onto ice. The mixture was brought to pH 10 with 10% NaOH and stirred for 10 min. The solution was adjusted to pH 5 with 5% HCl and the mixture was transferred into a separatory funnel. The bottom organic layer was separated and extracted with deionized water. The aqueous layers were combined, washed with dichloromethane and concentrated under vacuum until a slurry was obtained. The slurry was diluted with acetonitrile (100 mL) and a small amount of deionized water was added until all the salts were dissolved and two layers formed. The layers were transferred to a separatory funnel. The bottom light brownish layer was isolated and diluted with a deionized water 1 mL of the solution was taken, diluted with CH₃CN (0.1 mL) and formic acid (0.1 mL) and was loaded on a 250×21 mm 10 micron C18 column. Elution with deionized water and acetonitrile (2% acetonitrile 0-5 min; linear gradient 2% acetonitrile-50% acetonitrile 5-23 min) gave the desired 4-(2'-pyridyldithio)-2-sulfo-butanoic acid (IV) (R_t=11 min). Evaporation of solvent under vacuum gave 288 mg of desired product as light brownish oil. The top CH₃CN layer was less clean than the lower brownish layer however additional product could be isolated from the top layer as follows. Solvent was removed under vacuum, residue was taken up in CH₃CN, H₂O and HCOOH (10:10:1), and loaded on a 250×21 mm 10 micron C18 column. The column was eluted with CH₃CN/H₂O (2% CH₃CN, 0-5 minutes; linear gradient 2% to 28% CH₃CN, 5-20 minutes; 28-90% CH₃CN, 20-20:30 min; 90% CH₃CN, 20:30-25:30 minutes; 90-2% CH₃CN, 25:30-26 minutes; 2% CH₃CN, 26-28 minutes) to give an additional 79 mg of (IV). ¹H NMR (400 Hz, D₂O): δ 8.55 (d, J=6.0 Hz, 1H), 8.31 (t, J=8.0 Hz, 1H), 8.16 (d, J=8.4 Hz, 1H), 7.71 (t, J=7.2 Hz, 1H), 3.83 (dd, J₁=9.2 Hz, J₂=5.2 Hz, 1H), 3.01-2.87 (m, 2H), 2.34-2.21 (m, 2H); ¹³C NMR (100 Hz, D₂O): 170.8, 155.8, 145.6, 142.7, 125.8, 124.1, 64.0, 35.9, 27.3. MS (ESI) m/z 307.7 (M-1).

Example 3

Alternative synthesis of 4-(2'-pyridyldithio)-2-sulfo-butanoic acid (IV) with addition of base in the reaction

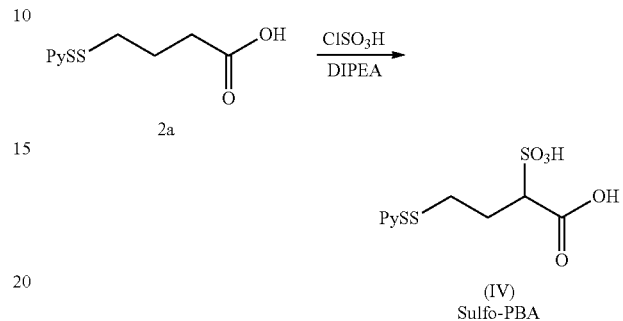

(IV)
Sulfo-PBA 4-(2-pyridyldithio)butanoic acid (2a) (102 mg, 0.45 mmol) was coevaporated with 1,2-dichloroethane (2×6 ml), redissolved in 6 ml of 1,2-dichloroethane and placed on preheated 75° C. oil bath. Chlorosulfonic acid (100 μL, 1.34 mmol) and N-ethyl-N-isopropylpropan-2-amine (117 μL, 0.67 mmol) were added and the mixture was heated with stirring at 75° C. for 15 min. Another aliquot of chlorosulfonic acid (80 μl, 1.19 mmol) and DIPEA (63 μL, 0.36 mmol) was then added and the reaction was heated at 75° C. for an additional 20 min. Analysis by HPLC indicated that the reaction was complete. The mixture was cooled in an ice bath and concentrated aqueous Na₂CO₃ added to pH 11, stirred for 10 min, neutralized with H₃PO₄ to pH 7.0, concentrated, and purified on a C-18 column eluted with a gradient from 100% of water (0.5% acetic acid) to 75% water (0.5% acetic acid)/25% of MeOH to afford of 4-(2'-pyridyldithio)-2-sulfo-butanoic acid (IV) (67 mg, 0.217 mmol, 48.7% yield). ¹H NMR (D₂O) 8.41 (dd, 1H, J=1.5, 4.9 Hz), 7.91~7.86 (m, 2H), 7.33~7.30 (m, 1H), 3.75 (dd, 1H, J=5.1, 9.6), 3.00~2.94 (m, 1H), 2.86~2.79 (m, 1H), 2.33~2.26 (m, 2H); ¹³C NMR 176.60, 160.28, 150.60, 140.27, 123.39, 122.92, 69.07, 37.56, 29.45; ESI MS m/z −307.8 (M-H).

Example 4

Preparation of N-succinimidyl 4-(2'-pyridyldithio)-2-sulfobutanoate (V) (sulfo-SPDB)

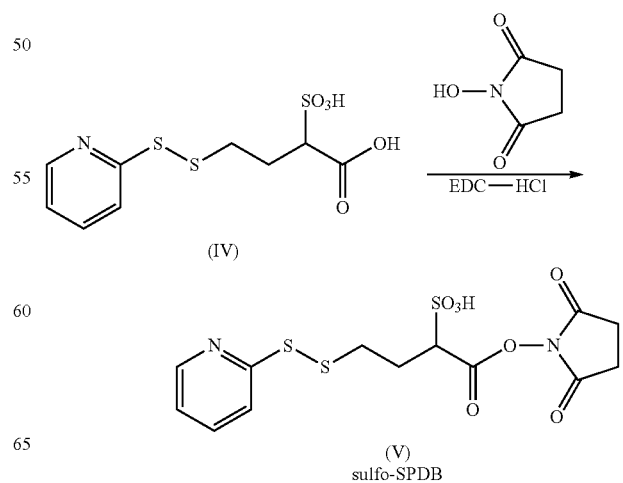

(V)
sulfo-SPDB 4-(2'-pyridyldithio)-2-sulfo-butanoic acid (IV) (245 mg, 0.792 mmol), EDC-HCl (345 mg, 2.222 mmol) and 1-hydroxypyrrolidine-2,5-dione (120 mg, 1.043 mmol) were stirred in DMA (8 mL) overnight and evaporated. The product was purified by silica gel chromatography eluting with a gradient of MeOH/CH$_2$Cl$_2$/HOAc (1:10:0.5% to 1:5:0.5%) to afford N-succinimidyl 4-(2'-pyridyldithio)-2-sulfobutanoate (V) (sulfo-SPDB). (258 mg, 0.635 mmol, 80% yield).

Example 5

Preparation of N-succinimidyl 4-(2'-pyridyldithio)-2-sulfobutanoate sodium salt (Vb) (sulfo-SPDB Na salt)

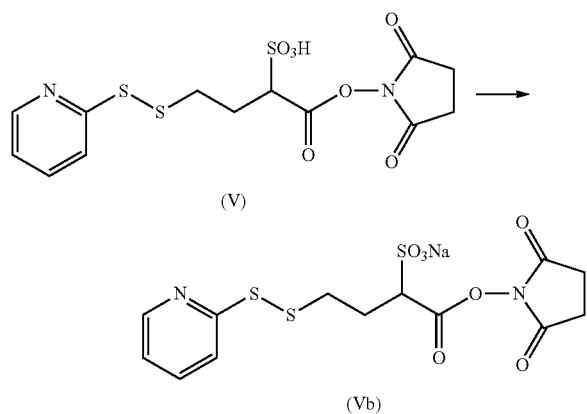

To a solution of N-succinimidyl 4-(2'-pyridyldithio)-2-sulfobutanoate (24 mg, 0.059 mmol) generated from silica gel column chromatography in cold DMA (0.5 mL) was added aqueous NaH$_2$PO$_4$, (1.0 M, 2 mL, pH 5.5. The mixture was stirred on ice for 2-3 min, evaporated under vacuum. The solid was suspended in 3 ml of DMA (3 mL), run through silica gel column eluted with 100% DMA. The fractions were pooled, evaporated and then crystallized with MeOH/EtOH/toluene/hexane to afford the sodium salt of N-succinimidyl 4-(2'-pyridyldithio)-2-sulfobutanoate (18 mg, 0.042 mmol, 71.2% yield). $^1$H NMR (DMF-d7) 8.49 (d, 1H, J=4.0 Hz), 7.88 (m, 2H), 7.27 (m, 1H), 4.05 (dd, 1H, J=5.0, 9.4 Hz), 3.17~3.08 (m, 2H), 2.92 (s, 4H), 2.56 (m, 1H), 2.46 (m, 1H); $^{13}$C NMR 171.16, 166.61, 160.65, 150.66, 138.81, 122.14, 120.37, 62.61, 36.63, 26.60; ESI MS m/z −404.7 (M-Na).

Example 6

Preparation of N-succinimidyl 4-(2'-pyridyldithio)-2-sulfobutanoate (V) (sulfo-SPDB)

1. The Synthesis of 2-Sulfo-PBA:
To a solution of 4-(pyridin-2-yldisulfanyl)butanoic acid (725 mg, 3.16 mmol) and 1,2-di(pyridin-2-yl)disulfane (700 mg, 3.18 mmol) in 15 ml of DCE (1,2-dichloroethane) at 75° C. was added chlorosulfuric acid (300 µL, 4.51 mmol). After stirring for 20 min at 75° C., another portion of chlorosulfuric acid (300 µL, 4.51 mmol) was added. The mixture was allowed to stir at 75° C. for 20 min, then another portion of chlorosulfuric acid (200 µL, 3.0 mmol) was added. Again 25 min later, the final portion of chlorosulfuric acid (200 µL, 3.0 mmol) was added and the mixture was stirred for further 25 min. The mixture was immediately cooled on ice bath, neutralized with 1M NaOH to pH ~7, diluted with EtOAc/Hexane (1:1), separated, and the organic layer was washed with pure water (3×25 ml) while the generated each of aqueous layer was washed with EtOAc/Hexane (1:1, 35 ml). The aqueous layers were combined, acidified with HCl/HOAc to pH 3~4, concentrated to ~10 ml, diluted with MeCN (100 ml), sonicated (or quickly stirred) for 1 h, filtered, and the resulting pellet washed with water/MeCN (1:10). The solution was then concentrated and purified on a SiO$_2$ cartridge (40 g) eluting with water/MeCN/HOAc (1:10:0.01). To the pooled fractions containing the product, DMF (~5 ml) was added and evaporated to dryness to afford 4-(pyridin-2-yldisulfanyl)-2-sulfobutanoic acid (295 mg, 0.954 mmol, 30.2% yield).

2. The Synthesis of Sulfo-SPDB Linker:
To a solution of 4-(pyridin-2-yldisulfanyl)-2-sulfobutanoic acid (0.292 mg, 0.944 µmol) in DMA (8 mL) was added 1-hydroxypyrrolidine-2,5-dione (0.120 mg, 1.043 µmol) and N1-((ethylimino)methylene)-N3,N3-dimethylpropane-1,3-diamine (EDC, 0.647 mg, 4.17 µmol). The reaction mixture was stirred overnight, evaporated and purified on a SiO$_2$ cartridge (40 g) eluting with a mixture of Acetone/DCM/HOAc (4:1:0.01). Product containing fractions were pooled, evaporated and solidified with EtOH/Tol/Hexane to afford 1-(2,5-dioxopyrrolidin-1-yloxy)-1-oxo-4-(pyridin-2-yldisulfanyl)butane-2-sulfonic acid (sulfo-SPDB, 0.270 mg, 0.664 µmol, 70.4% yield).

Example 7

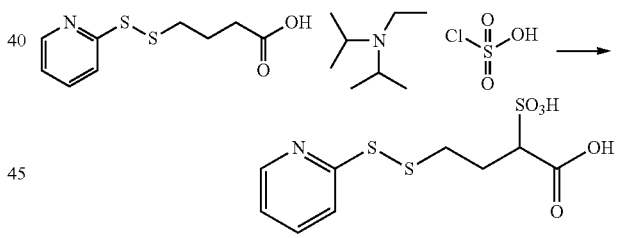

4-(pyridin-2-yldisulfanyl)butanoic acid (102 mg, 0.445 mmol) was coevaporated with 1,2-dichloroethane, (2×6 ml) (to remove moisture) and re-dissolved in 6 ml of 1,2-dichloroethane. The resulting solution was then placed in a preheated oil bath (75~80° C.). To this solution, sulfurochloridic acid (100 µL, ~3 eq) was added and the resulting mixture was stirred for 5~8 min. DIPEA (117 iµL, 1.5 eq) was then added (to precipitate the product) and the resulting mixture was stirred for 5 min. Another portion of sulfurochloridic acid (40 ul, 1.33 eq) was added and the mixture was stirred for ~15 min, followed by addition of DIPEA (63 µL, 0.81 eq) and stirred for 5 min. A third portion of sulfurochloridic acid (40 ul, 1.33 eq) was added and the mixture was stirred for 15~20 min. The resulting mixture was removed from the oil bath and cooled (on ice bath). Aqueous NaOH (0.5 M) or concentrated Na$_2$CO$_3$ was added to raise the pH ~12 and the reaction mixture was stirred for 10 min. The organic phase was separated, washed with water (2×10 ml), and neutralized with H₃PO₄ to pH 7. The organic phase was then concentrated to ~5 ml and acidified with HCl to pH ~4. The crude product was purified by passing through a C-18 column using eluting with a gradient of 100% water (containing 0.5% HAc) to 75% of water (containing 0.5% HAc)/25% of MeOH. Fractions containing the desired product (eluted out at 5-10% of MeOH) were pooled, evaporated to afford 4-(pyridin-2-yldisulfanyl)-2-sulfobutanoic acid (67 mg, 0.217 mmol, 48.7% yield). ¹H NMR (D₂O) 8.41 (dd, 1H, J=1.5, 4.9 Hz), 7.89 (m, 2H), 7.31 (m, 1H), 3.75 (dd, 1H, J=5.1, 9.6), 2.97 (m, 1H), 2.82 (m, 1H), 2.28 (m, 2H); ¹³C NMR 176.60, 160.28, 150.60, 140.27, 123.39, 122.92, 69.07, 37.56, 29.45; ESI MS m/z −307.8 (M-H).

Alternative procedure: 4-(pyridin-2-yldisulfanyl)butanoic acid (106 mg, 0.462 mmol) was coevaporated with 1,2-dichloreoethane (2×5 ml), redissolved in 5 ml of 1,2-dichloreoethane and placed in a preheated 75° C. oil bath. To this solution, sulfurochloridic acid (154 μL, 2.311 mmol) and N-ethyl-N-isopropylpropan-2-amine (161 μL, 0.924 mmol) were added. The mixture was placed in the pre-heated 75° C. oil bath for 45 min. Another portion of sulfurochloridic acid (45 μL, 0.675 mmol) was added and the reaction was heated at 75° C. for 1 more hour until the reaction was completed (monitored by HPLC). To the mixture was added concentrated Na₂CO₃ until pH 11. The resulting mixture was stirred for 10 min, neutralized with H₃PO₄ to pH 7.5 and concentrated. The crude product was purified by HPLC on a C-18 column eluting with a gradient of 100% of water (0.5% HAc) to 80% water (0.5% HAc)/20% of MeOH to afford 4-(pyridin-2-yldisulfanyl)-2-sulfobutanoic acid (63 mg, 0.204 mmol, 44.1% yield).

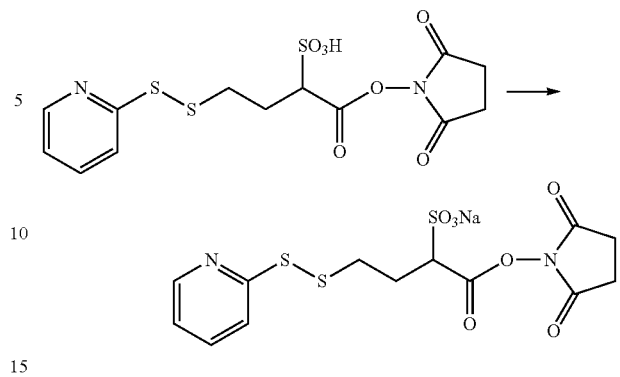

To 1-(2,5-dioxopyrrolidin-1-yloxy)-1-oxo-4-(pyridin-2-yldisulfanyl)butane-2-sulfonic acid (24 mg, 0.059 mmol) generated from SiO₂ column chromatography (eluted with 1:10:0.5% to 1:5:0.5% of MeOH/CH₂Cl₂/HAc) was added cold 0.5 ml of DMA and 2 ml of 1.0 M NaH₂PO₄, pH 5.5. The mixture was stirred on an ice bath for 2~3 min, evaporated using an oil pump (with no heat, free dry style). The resulting solid was suspended in 3 ml of DMA and passed through a silica gel column eluting with 100% DMA. The fractions were pooled, evaporated and then crystallized with MeOH/EtOH/Toluene/Hexane to afford sodium 1-(2,5-dioxopyrrolidin-1-yloxy)-1-oxo-4-(pyridin-2-yldisulfanyl)butane-2-sulfonate (18 mg, 0.042 mmol, 71.2% yield). ¹H NMR (DMF-d7) 8.49 (d, 1H, J=4.0 Hz), 7.88 (m, 2H), 7.27 (m, 1H), 4.05 (dd, 1H, J=5.0, 9.4 Hz), 3.17~3.08 (m, 2H), 2.92 (s, 4H), 2.56 (m, 1H), 2.46 (m, 1H); ¹³C NMR 171.16, 166.61, 160.65, 150.66, 138.81, 122.14, 120.37, 62.61, 36.63, 26.60; ESI MS m/z −404.7 (M-Na);

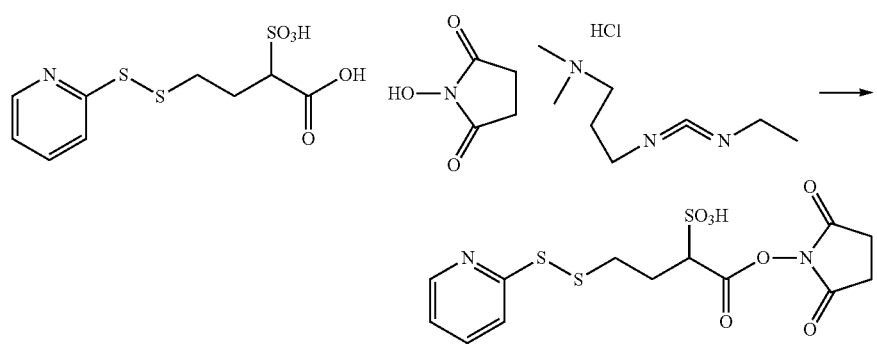

A mixture of 4-(pyridin-2-yldisulfanyl)-2-sulfobutanoic acid (245 mg, 0.792 mmol), N1-((ethylimino)methylene)-N3,N3-dimethylpropane-1,3-diamine (345 mg, 2.222 mmol) and 1-hydroxypyrrolidine-2,5-dione (120 mg, 1.043 mmol) were stirred in 8 ml of DMA overnight. The resulting solution was evaporated and the residue was purified on a silica column using MeOH/CH₂Cl₂ (1:10 to 1:5) containing 0.5% acetic acid as eluting solvent to afford 1-(2,5-dioxopyrrolidin-1-yloxy)-1-oxo-4-(pyridin-2-yldisulfanyl)butane-2-sulfonic acid (258 mg, 0.635 mmol, 80% yield).

Example 8

Instruments and Methods

1. X-Ray Powder Diffraction (XRPD)

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v11.0.0.2 or v13.0.0.2.

Samples were run under ambient conditions as flat plate specimens using powder as received. The sample was gently packed into a cavity cut into polished, zero-background (510) silicon wafer. The sample was rotated in its own plane during analysis. The details of the data collection are:
Angular range: 2 to 42° 2θ
Step size: 0.05° 2θ
Collection time: 0.5 s/step
For Crystalline Form 3 the angular range was of 3 to 30° 2θ.

2. Differential Scanning Calorimetry (DSC)

DSC data were collected on a Mettler DSC 823e equipped with a 34 position auto-sampler. The instrument was calibrated for energy and temperature using certified indium. Typically 0.5-2.0 mg of each sample, in a pin-holed aluminium pan, was heated at 10° C./min from 25° C. to 240° C. A nitrogen purge at 50 ml/min was maintained over the sample. The instrument control and data analysis software was STARe v9.20.

3. Thermo-Gravimetric Analysis (TGA)

TGA data were collected on a Mettler TGA/SDTA 851e equipped with a 34 position auto-sampler. The instrument was temperature calibrated using certified indium. Typically 5-10 mg of each sample was loaded onto a pre-weighed aluminium crucible and was heated at 10° C./min from ambient temperature to 350° C. A nitrogen purge at 50 ml/min was maintained over the sample. The instrument control and data analysis software was STARe v9.20.

4. Gravimetric Vapour Sorption (GVS)

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 10 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.0.0.7.

TABLE 5

Method Parameters for SMS DVS Intrinsic Experiments

| Parameters | Values |
| --- | --- |
| Adsorption—Scan 1 | 40-90 |
| Desorption/Adsorption—Scan 2 | 90-0, 0-40 |
| Intervals (% RH) | 10 |
| Number of Scans | 2 |
| Flow rate (ml/min) | 200l |
| Temperature (° C.) | 25 |

TABLE 5-continued

Method Parameters for SMS DVS Intrinsic Experiments

| Parameters | Values |
| --- | --- |
| Stability (° C./min) | 0.2 |
| Sorption Time (hours) | 6 hour time out |

The sample was recovered after completion of the isotherm and re-analysed by XRPD.

5. Ion Chromatography (IC)

Data were collected on a Metrohm 861 Advanced Compact IC (for anions) using IC Net software v2.3. Accurately weighed samples were prepared as stock solutions in an appropriate dissolving solution and diluted appropriately prior to testing. Quantification was achieved by comparison with standard solutions of known concentration of the ion being analysed.

TABLE 6

IC Method Parameters for Anion Chromatography

| Type of method | Anion exchange |
| --- | --- |
| Column | Metrosep A Supp 5—250 (4.0 × 250 mm) |
| Column Temperature (° C.) | Ambient |
| Injection (μl) | 10 |
| Detection | Conductivity detector |
| Flow Rate (ml/min) | 0.7 |
| Eluent | 32 mM sodium carbonate, 1.0 mM sodium hydrogen carbonate in 5% aqueous acetone |

Example 9

Crystallization Procedures for Crystalline Forms 1, 2a, 2b and 3

1. Crystalline Form 1

531 mg of the DIPEA salt of sulfo-SPDB (sulfo-SPDB•0.6DIPEA) was slurried in 1 ml of Acetone/H$_2$O (95/5 v/v) and magnetically stirred at about −20° C. for 16 hours. The sample was filtered on a 0.45 μm Whatman Autocup and washed with 2 ml of acetone. The sample was dried at room temperature for 6 hours and weighed. 113 mg of Crystalline Form 1 was crystallized (Yield: 35%).

2. Crystalline Form 2a a) Removing DIPEA from the Sulfo-SPDB DIPEA Salt Using Cation Exchange Media.

1.09 g of Crystalline Form 1 was obtained from crystallization of 5.92 g of the DIPEA salt of sulfo-SPDB (sulfo-SPDB•0.6DIPEA) in 20 ml of acetone at about −20° C. Crystalline Form 1 was filtered (Yield: 29%) and the liquor was carefully retrieved (liquor 1).

Liquor 1 was concentrated under reduced pressure to afford 4.84 g of amorphous Sulfo-SPDB DIPEA salt. The salt was dissolved in 50 ml of acetonitrile and eluted on 13.7 g of Amberlyst® 15 (Sigma-Aldrich, 216380—dry, moisture≤1.5%, 8 eq.) with about 220 ml of acetonitrile (liquor 2). The resin was initially washed and equilibrated in acetonitrile and water and then equilibrated with acetonitrile before use.

Liquor 2 was concentrated under reduced pressure to give 1.37 g of amorphous Sulfo-SPDB (Yield: 37%).

b) Crystallization Procedure

Amorphous Sulfo-SPDB (1.37 g) was diluted in 10 ml of acetone, seeded with 21 mg of Crystalline Form 1 and placed under magnetic stirring at −20° C. for 3 hours. The sample was filtered on a 0.45 μm Whatman Autocup and the vial was washed with 150 ml of acetone and 150 ml of TBME. The sample was dried at room temperature for 16 hours and weighed. 722 mg of Crystalline Form 2a was recovered (Yield: 64%).

3. Crystalline Form 3

79 mg of the supplied DIPEA salt of sulfo-SPDB (sulfo-SPDB·0.6DIPEA) was slurried in 200 μl of Acetone/H₂0 (90/10 v/v). 110 μl of a stock solution of HCl in Acetone/H₂0 (90/10) v/v (1.0 eq.) was added to the slurry at room temperature. The sample was observed to become a light slurry and was placed under magnetic stirring for 16 hours at −20° C. The sample was filtered on a 0.45 μm Whatman Autocup and washed with 1 ml of acetone. The sample was dried at room temperature for 6 hours and weighed. 43 mg of Crystalline Form 3 was recovered (Yield: 84%).

Example 10

Preparation of Crystalline Form 2b from Crystalline Form 3

Crystalline Form 2b was also obtained from Crystalline Form 3 by dehydration at 0% RH using P₂O₅ as desiccant or by drying under vacuum at 30° C. for 24 hours.

What is claimed is:

1. A process for the preparation of a compound of formula (III):

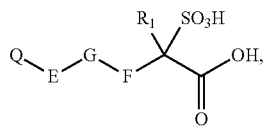

or a salt thereof, comprising the step of reacting a compound of formula (II):

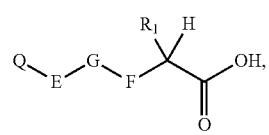

or a salt thereof, with a sulfonating agent in the presence of a base, wherein:
Q represents a disulfide group selected from alkyl disulfide, phenyl disulfide, ortho or para-nitrophenyl disulfide, 2,4-dintrophenyl disulfide, pyridyl disulfide, nitropyridyl disulfide; a maleimido group or a haloacetyl group;
G and F are both absent;
E represents a linear or branched alkyl bearing 1 to 4 carbon atoms; and $R_1$ is —H or a linear, branched or cyclic alkyl, alkenyl or alkynyl bearing 1 to 10 carbon atoms.

2. The process of claim 1, wherein the sulfonating agent is chlorosulfonic acid or sulfur trioxide; and the base is triethyl amine, diisopropylethyl amine or tributyl amine.

3. The process of claim 1, wherein the sulfonating agent is chlorosulfonic acid and the base is diisopropylethyl amine.

4. The process of claim 1, wherein E is —CH₂—CH₂— and $R_1$ is H.

5. The process of claim 1, wherein Q is pyridyl disulfide.

6. A process for the preparation of a compound of formula (IV):

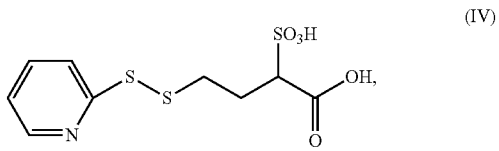 [SMILES: O=C(O)C(CCSSc1ccccn1)S(=O)(=O)O]

or a salt thereof, comprising the step of reacting a compound of formula (2a):

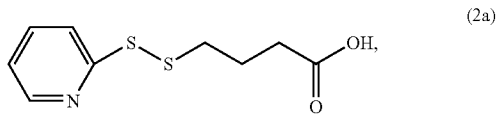 [SMILES: O=C(O)CCCSSc1ccccn1]

or a salt thereof, with a sulfonating agent in the presence of a base.

7. The process of claim 6, wherein the sulfonating agent is chlorosulfonic acid or sulfur trioxide and the base is triethyl amine, diisopropylethyl amine or tributyl amine.

8. The process of claim 6, wherein the sulfonating agent is chlorosulfonic acid and the base is diisopropylethyl amine.

9. The process of claim 8, wherein the sulfonating reaction is carried out in the presence of 1,2-di(pyridin-2-yl)disulfane (PySSPy).

10. The process of claim 9, wherein about 0.5 equivalent of PySSPy is present.

11. The process of claim 6, wherein the process further comprises the step of purifying the compound of formula (IV) obtained by the reaction.

12. The process of claim 11, wherein the compound of formula (IV) is purified by reverse phase chromatography using a silica column.

13. The process of claim 1, further comprising reacting the compound of formula (III) or a salt thereof with a hydroxy or mercapto compound to form a compound of formula (I),

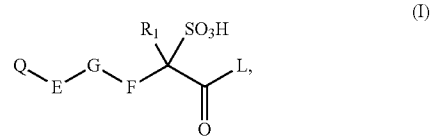

or a salt thereof, wherein:
C(=O)L represents a reactive ester or thioester group selected from N-hydroxysuccinimide ester, N-hydroxy sulfosuccinimide ester, nitrophenyl ester, tetrafluoro phenyl ester, pentafluorophenyl ester, a thiopyridyl ester and a thionitrophenyl ester.

14. The process of claim 13, wherein the reaction between the compound of formula (III) and the hydroxy or mercapto compound is carried out in the presence of a coupling agent selected from N,N'-dicyclohexylcarbodiimide (DCC), 1-ethyl-3-(3-dimethylaminopropyl)carbodiimide (EDC), N,N'-diisopropyl carbodiimide (DIC) and 1-ethoxycarbonyl-2-ethoxy-1,2-dihydroquinoline (EEDQ).

15. The process of claim 14, wherein the coupling agent is EDC.

16. The process of claim 13, wherein the reactive ester is N-hydroxysuccinimide ester.

17. The process of claim 13, wherein E is —$CH_2$—$CH_2$— and $R_1$ is H.

18. The process of claim 13, wherein Q is pyridyl disulfide.

19. A process for the preparation of a compound represented by formula (V):

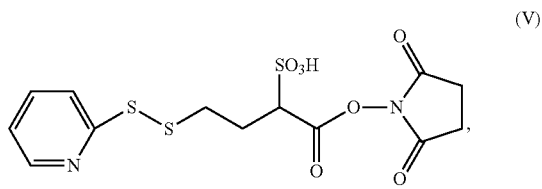 [SMILES: O=C(ON1C(=O)CCC1=O)C(CCSSc1ccccn1)S(=O)(=O)O]

or a salt thereof, comprising the steps of:
a) reacting a compound of formula (2a):

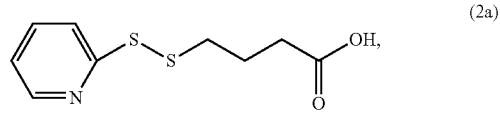 [SMILES: O=C(O)CCCSSc1ccccn1]

or a salt thereof, with a sulfonating agent in the presence of a base to form a compound of formula (IV):

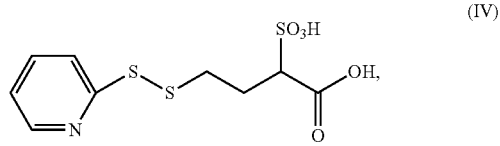 [SMILES: O=C(O)C(CCSSc1ccccn1)S(=O)(=O)O]

or a salt thereof; and b) reacting the compound of formula (IV), or a salt thereof, with N-hydroxysuccinimide to form the compound of formula (V).

20. The process of claim 19, wherein the sulfonating agent is chlorosulfonic acid or sulfur trioxide and the base is the base is triethyl amine, diisopropylethyl amine or tributyl amine.

21. The process of claim 19, wherein the sulfonating agent is chlorosulfonic acid and the base is diisopropylethyl amine.

22. The process of claim 21, wherein the sulfonating reaction is carried out in the presence of PySSPy.

23. The process of claim 22, wherein about 0.5 equivalent of PySSPy is present.

24. The process of claim 19, wherein the reaction between the compound of formula (IV) and N-hydroxysuccinimide is carried out in the presence of a coupling agent selected from N,N'-dicyclohexylcarbodiimide (DCC), 1-ethyl-3-(3-dimethylaminopropyl)carbodiimide (EDC), N,N'-diisopropyl carbodiimide (DIC) and 1-ethoxycarbonyl-2-ethoxy-1,2-dihydroquinoline (EEDQ).

25. The process of claim 24, wherein the coupling agent is EDC.

26. The process of claim 19, wherein the reaction between the compound of formula (IV) and N-hydroxysuccinimide is carried in the presence of a base.

27. The process of claim 26, wherein the base is diisopropylethylamine (DIPEA).

28. The process of claim 19, wherein the process comprises the steps of:
a) reacting the compound of formula (2a) or a salt thereof with chlorosulfonic acid to form the compound of formula (IV); and
b) reacting the compound of formula (IV) with N-hydroxysuccinimide in the presence of EDC to form the compound of formula (V).

29. The process of claim 19, further comprising the step of purifying the compound of formula (IV) or a salt thereof.

30. The process of claim 29, wherein the compound of formula (IV) or a salt thereof is purified by reverse phase chromatography using a silica column.

31. The process of claim 28, further comprising the step of purifying the compound of formula (V) or a salt thereof.

32. The process of claim 31, wherein the compound of formula (V) or a salt thereof is purified by reverse phase chromatography using a silica column.

33. The process of claim 31, wherein the compound of formula (V) or a salt thereof is purified by crystallization.

* * * * *